United States Patent
Yang et al.

(10) Patent No.: US 10,948,401 B2
(45) Date of Patent: Mar. 16, 2021

(54) SPINNING APPARATUS FOR MEASUREMENT OF CHARACTERISTICS RELATING TO MOLECULES

(71) Applicants: Children's Medical Center Corporation, Boston, MA (US); President and Fellows of Harvard College, Cambridge, MA (US)

(72) Inventors: Darren Yang, Somerville, MA (US); Andrew Ward, Boston, MA (US); Wesley Philip Wong, Cambridge, MA (US); Kenneth Anders Halvorsen, Glenmont, NY (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 178 days.

(21) Appl. No.: 16/079,995

(22) PCT Filed: Feb. 24, 2017

(86) PCT No.: PCT/US2017/019318
§ 371 (c)(1),
(2) Date: Aug. 24, 2018

(87) PCT Pub. No.: WO2017/147398
PCT Pub. Date: Aug. 31, 2017

(65) Prior Publication Data
US 2019/0064056 A1    Feb. 28, 2019

Related U.S. Application Data

(60) Provisional application No. 62/299,711, filed on Feb. 25, 2016.

(51) Int. Cl.
*G01N 21/07* (2006.01)
*B04B 15/00* (2006.01)
(Continued)

(52) U.S. Cl.
CPC .............. *G01N 21/07* (2013.01); *B82Y 15/00* (2013.01); *C12Q 1/68* (2013.01); *C12Q 1/6816* (2013.01);
(Continued)

(58) Field of Classification Search
CPC .......................... C12Q 1/68; C12Q 2523/303; C12Q 2525/30; C12Q 1/6816; B04B 13/00;
(Continued)

(56) References Cited

U.S. PATENT DOCUMENTS 3,009,388 A    11/1961 Polanyi
3,727,066 A     4/1973 Louderback et al.
(Continued)

FOREIGN PATENT DOCUMENTS

CN    104568752 A    4/2015
EP    0 123 178 A2   10/1984
(Continued)

OTHER PUBLICATIONS

Supplementary Partial European Search Report dated Dec. 6, 2019, for Application No. EP 17757284.9.
(Continued)

*Primary Examiner* — Jennifer Wecker
(74) *Attorney, Agent, or Firm* — Wolf, Greenfield & Sacks, P.C.

(57) ABSTRACT

An apparatus for measuring a characteristic of a sample using a centrifuge and optical components is disclosed. The centrifuge may be a standard benchtop centrifuge. The
(Continued)

optical components may be sized and dimensioned to fit, along with the sample, inside the centrifuge.

17 Claims, 20 Drawing Sheets

Specification includes a Sequence Listing.

(51) Int. Cl.
| | |
|---|---|
| G01N 33/557 | (2006.01) |
| B82Y 15/00 | (2011.01) |
| G01N 33/53 | (2006.01) |
| C12Q 1/68 | (2018.01) |
| C12Q 1/6816 | (2018.01) |
| G01N 33/543 | (2006.01) |
| G01N 15/14 | (2006.01) |
| G01N 15/00 | (2006.01) |
| G01N 15/10 | (2006.01) |
| B04B 13/00 | (2006.01) |
| B04B 15/02 | (2006.01) |

(52) U.S. Cl.
CPC ......... *G01N 15/1434* (2013.01); *G01N 33/53* (2013.01); *G01N 33/543* (2013.01); *G01N 33/557* (2013.01); *B04B 13/00* (2013.01); *B04B 15/02* (2013.01); *G01N 2015/0038* (2013.01); *G01N 2015/0065* (2013.01); *G01N 2015/1006* (2013.01); *G01N 2201/021* (2013.01); *G01N 2201/0423* (2013.01); *G01N 2201/0693* (2013.01); *G01N 2203/0089* (2013.01)

(58) Field of Classification Search
CPC .... B04B 15/02; B82Y 15/00; G01N 15/1434; G01N 2015/0038; G01N 2015/0065; G01N 2015/1006; G01N 21/07; G01N 2201/021; G01N 2201/0423; G01N 2201/0693; G01N 2203/0089; G01N 33/53; G01N 33/543; G01N 33/557

See application file for complete search history.

(56) References Cited

U.S. PATENT DOCUMENTS

| | | | |
|---|---|---|---|
| 4,032,066 A | | 6/1977 | Wright |
| 5,356,365 A | * | 10/1994 | Brierton .................. B04B 15/02 494/14 |
| 5,712,710 A | | 1/1998 | Karakus et al. |
| 5,958,703 A | | 9/1999 | Dower et al. |
| 6,001,310 A | | 12/1999 | Shaffer et al. |
| 6,143,183 A | | 11/2000 | Wardwell et al. |
| 6,201,639 B1 | | 3/2001 | Overbeck |
| 6,654,102 B1 | | 11/2003 | Modares et al. |
| 7,052,650 B2 | | 5/2006 | Strick et al. |
| 8,491,454 B2 | | 7/2013 | Wong et al. |
| 8,795,143 B2 | | 8/2014 | Wong et al. |
| 9,354,189 B2 | | 5/2016 | Wong et al. |
| 9,897,597 B2 | | 2/2018 | Shih et al. |
| 10,265,705 B2 | | 4/2019 | Wong et al. |
| 2002/0147094 A1 | * | 10/2002 | Dolecek ................ B04B 5/0442 494/9 |
| 2002/0177144 A1 | | 11/2002 | Remacle et al. |
| 2003/0077839 A1 | | 4/2003 | Takei |
| 2003/0155527 A1 | | 8/2003 | Natori |
| 2003/0166262 A1 | | 9/2003 | Strick et al. |
| 2004/0017567 A1 | | 1/2004 | Loicht et al. |
| 2005/0194325 A1 | | 9/2005 | Moore et al. |
| 2007/0155017 A1 | | 7/2007 | Wyatt |
| 2007/0231796 A1 | | 10/2007 | Majda |
| 2007/0238598 A1 | | 10/2007 | Kim et al. |
| 2009/0118140 A1 | | 5/2009 | Suzara |
| 2010/0137120 A1 | * | 6/2010 | Wong ............... G01N 33/54313 494/10 |
| 2012/0058008 A1 | | 3/2012 | Corbett et al. |
| 2012/0149129 A1 | | 6/2012 | Pai et al. |
| 2012/0238738 A1 | | 9/2012 | Hendrickson |
| 2013/0005049 A1 | | 1/2013 | Mao et al. |
| 2013/0123089 A1 | | 5/2013 | Johns et al. |
| 2013/0130884 A1 | * | 5/2013 | Wong .................. G02B 21/362 494/10 |
| 2013/0225429 A1 | | 8/2013 | Curry |
| 2013/0288349 A1 | | 10/2013 | Wong et al. |
| 2015/0122977 A1 | * | 5/2015 | Halvorsen .......... G01N 15/1436 250/214.1 |
| 2016/0116490 A1 | * | 4/2016 | Knutson ................ G01N 33/80 506/9 |
| 2016/0243560 A1 | | 8/2016 | Wong et al. |
| 2017/0045506 A1 | | 2/2017 | Shih et al. |
| 2018/0306783 A1 | | 10/2018 | Shih et al. |
| 2018/0364225 A1 | | 12/2018 | Nathwani et al. |

FOREIGN PATENT DOCUMENTS

| | | |
|---|---|---|
| EP | 0 589 556 A2 | 3/1994 |
| JP | 11258081 A | 9/1999 |
| WO | WO 2008/112980 A2 | 9/2008 |
| WO | WO 2010/065477 A2 | 6/2010 |
| WO | WO 2011/153211 A1 | 12/2011 |
| WO | WO 2012/012037 A1 | 1/2012 |
| WO | WO 2013/059044 A1 | 4/2013 |
| WO | WO 2013/067489 A1 | 5/2013 |
| WO | WO 2015/166399 A1 | 11/2015 |

OTHER PUBLICATIONS

International Search Report and Written Opinion dated Jun. 7, 2017 in connection with International Application No. PCT/US2017/019318.
International Preliminary Report on Patentability dated Sep. 7, 2018 for Application No. PCT/U52017/019318.
International Preliminary Report on Patentability for Application No. PCT/US2009/066 154 dated Jun. 16, 2011.
International Search Report and Written Opinion for Application No. PCT/US2009/066154 dated Jul. 27, 2010.
European Examination Report for European Application No. EP 11728725.0 dated Jun. 16, 2016.
International Preliminary Report on Patentability for Application No. PCT/US2011/038716 dated Dec. 4, 2012.
International Search Report and Written Opinion for Application No. PCT/US2011/038716 dated Aug. 29, 2011.
Extended European Search Report dated Nov. 10, 2017 for Application No. EP 15783027.4.
Extended European Search Report dated Nov. 8, 2019 for Application No. EP 19195115.1.
Invitation to Pay Additional Fees dated Aug. 13, 2015 for PCT/US2015/027290.
International Search Report and Written Opinion dated Oct. 28, 2015 for PCT/US2015/027290.
International Preliminary Report on Patentability dated Nov. 3, 2016 for PCT/US2015/027290.
Invitation to Pay Additional Fees dated Jan. 30, 2017 for PCT/US2016/065341.
International Search Report and Written Opinion dated Apr. 12, 2017 in connection with International Application No. PCT/US2016/065341.
International Preliminary Report on Patentability dated Jun. 21, 2018 in connection with International Application No. PCT/US2016/065341.
Ackbarow et al., Strength and robustness of protein materials. Encyclopedia of Nanoscience and Nanotechnology. 2011;23:349-87.
Al Bitar et al., Tarsal morphology and attachment ability of the codling moth *Cydia pomonella* L. (Lepidoptera, Tortricidae) to smooth surfaces. J Insect Physiol. Nov. 2009;55(11):1029-38. Epub Aug. 5, 2009.

(56) References Cited

OTHER PUBLICATIONS

Basle et al., Protein chemical modification on endogenous amino acids. Chem Biol. Mar. 26, 2010;17(3):213-27. doi: 10.1016/j.chembiol.2010.02.008.
Baumann et al., Ionic effects on the elasticity of single DNA molecules. Proc Natl Acad Sci U S A. Jun. 10, 1997;94(12):6185-90.
Block et al., Bead movement by single kinesin molecules studied with optical tweezers. Nature. Nov. 22, 1990;348(6299):348-52.
Bustamante et al., Ten years of tension: single-molecule DNA mechanics. Nature. Jan. 23, 2003;421(6921):423-7.
Chon et al., A von Willebrand factor-derived heparin-binding peptide regulates cell-substrate adhesive strength and chemokinesis behavior. Biochim Biophys Acta. Jan. 30, 2002;1542(1-3):195-208.
Claridge et al., Electrons, photons, and force: quantitative single-molecule measurements form physics to biology. ACS Nano. Feb. 22, 2011;5(2):693-729.
De Vlaminck et al., Magnetic forces and DNA mechanics in multiplexed magnetic tweezers. PLoS One. 2012;7(8):e41432. Epub Aug. 3, 2012.
Dessinges et al. Stretching single stranded DNA, a model polyelectrolyte. Phys Rev Lett. Dec. 9, 2002;89(24):248102(1-4), Epub Nov. 22, 2002.
Douglas et al. Self-assembly of DNA into nanoscale three-dimensional shapes. Nature 459, 414-418 (2009).
Evans et al., Chemically distinct transition states govern rapid dissociation of single L-selectin bonds under force. Proc Natl Acad Sci U S A. Mar. 27, 2001;98(7):3784-9. Epub Mar. 13, 2001.
Evans et al., Dynamic strength of molecular adhesion bonds. Biophys J. Apr. 1997;72(4):1541-55.
Evans, Probing the relation between force—lifetime—and chemistry in single molecular bonds. Annu Rev Biophys Biomol Struct. 2001;30:105-28.
Fazio et al., DNA curtains and nanoscale curtain rods: high-throughput tools for single molecule imaging. Langmuir. Sep. 16, 2008;24(18):10524-31. doi: 10.1021/la801762h. Epub Aug. 7, 2008.
Federle et al., Attachment forces of ants measured with a centrifuge: better 'wax-runners' have a poorer attachment to a smooth surface. J Exp Biol. Feb. 2000;203(Pt 3):505-12.
Fernandez et al., Force-clamp spectroscopy monitors the folding trajectory of a single protein. Science. Mar. 12, 2004;303(5664):1674-8.
Friedrich et al., The slow rotating centrifuge microscope NIZEMI—a versatile instrument for terrestrial hypergravity and space microgravity research in biology and materials science. J Biotechnol. Jun. 27, 1996;47(2-3):225-38.
Giessibl, Advances in atomic force microscopy. Rev Mod Phys. Jul. 29, 2003;75(3):949-83.
Greenleaf et al., High-resolution, single-molecule measurements of biomolecular motion. Annu Rev Biophys Biomol Struct. 2007;36:171-90.
Grier, A revolution in optical manipulation. Nature. Aug. 14, 2003;424(6950):810-6.
Ha, Single-molecule fluorescence resonance energy transfer. Methods. Sep. 2001;25(1):78-86.
Halvorsen et al., Massively parallel single-molecule manipulation using centrifugal force. Biophys J. Jun. 2, 2010;98(11):L53-5.
Halvorsen et al., Nanoengineering a single-molecule mechanical switch using DNA self-assembly. Nanotechnology. Dec. 9, 2011;22(49):494005. doi:10.1088/0957-4484/22/49/494005. Epub Nov. 21, 2011.
Hansen et al., Nanoswitch-linked immunosorbent assay (NLISA) for fast, sensitive, and specific protein detection. PNAS. Sep. 26, 2017;114(39):10367-10372. Supporting Information, 4 pages.
Harvey et al., A microscope-centrifuge. Science. Jul. 11, 1930;72(1854):42-4.
Heinrich et al., Imaging biomolecular interactions by fast three-dimensional tracking of laser-confined carrier particles. Langmuir. Feb. 19, 2008;24(4):1194-203. Epub Jan. 17, 2008.
Hummer et al., Free energy surfaces from single-molecule force spectroscopy. Acc Chem Res. Jul. 2005;38(7):504-13.
Janshoff et al., Force spectroscopy of molecular systems-single molecule spectroscopy of polymers and biomolecules. Angew Chem Int Ed. Sep. 15, 2000;39(18):3212-37.
Kellermayer et al., Folding-unfolding transitions in single titin molecules characterized with laser tweezers. Science.May 16, 1997;276(5315):1112-6.
Kim et al., A high-resolution magnetic tweezer for single-molecule measurements. Nucleic Acids Res. Nov. 2009;37(20):e136. doi: 10.1093/nar/gkp725. Epub Sep. 3, 2009.
Kim et al., A mechanically stabilized receptor-ligand flex-bond important in the vasculature. Nature. Aug. 19, 2010;466(7309):992-5. doi: 10.1038/nature09295.
Kim et al., Multiplexed single-molecule assay for enzymatic activity on flow-stretched DNA. Nat Methods. May 2007;4(5):397-9. Epub Apr. 15, 2007.
Koirala et al., Single-molecule mechanochemical sensing using DNA origami nanostructures. Angew Chem Int Ed Engl. Jul. 28, 2014;53(31):8137-41. doi: 10.1002/anie.201404043. Epub Jun. 26, 2014.
Koo et al., Co-regulation of cell adhesion by nanoscale RGD organization and mechanical stimulus. J Cell Sci. Apr. 1, 2002;115(Pt 7):1423-33.
Koussa et al., DNA nanoswitches: a quantitative platform for gel-based biomolecular interaction analysis. Nat. Methods. Feb. 1, 2015;12(2):123-6. Suppl Protocol, 4 pages. Epub Dec. 8, 2014.
Koussa et al., Protocol for sortase-mediated construction of DNA-protein hybrids and functional nanostructures. Methods. May 15, 2014;67(2):134-41. doi: 10.1016/j.ymeth.2014.02.020. Epub Feb. 22, 2014.
Lansdorp et al., A high-speed magnetic tweezer beyond 10,000 frames per second. Rev Sci Instrum. Apr. 2013;84(4):044301(1-5), doi:10.1063/1.4802678.
McClay et al., Intercellular recognition: quantitation of initial binding events. Proc Natl Acad Sci U S A. Aug. 1981;78(8):4975-9.
Mehta et al., Myosin-V is a processive actin-based motor. Nature. Aug. 5, 1999;400(6744):590-3.
Merkel et al., Energy landscapes of receptor-ligand bonds explored with dynamic force spectroscopy. Nature. Jan. 7, 1999;397(6714):50-3.
Monroe, The optical trap. Scientist. Aug. 29, 2005;19(16):48-52. Retrieved from the internet http://www.the-scientist.com/?articles.view/articleNo/16665/title/The-Optical-Trap/ on Jan. 28, 2013.
Nathwani et al., Multiplexed Mechanochemistry Assay. 60th Ann Mtg Biophys Soc. Mar. 1, 2016;2470-Pos;Board B614.
Nelson et al., Tethered particle motion as a diagnostic of DNA tether length. J Phys Chem B. Aug. 31, 2006;110(34):17260-7. Abstract only.
Neuman et al., Optical trapping. Rev Sci Instrum. Sep. 2004;75(9):2787-809.
Neuman et al., Single-molecule force spectroscopy: optical tweezers, magnetic tweezers and atomic force microscopy. Nat Methods. Jun. 2008;5(6):491-505.
Otto et al., Real-time particle tracking at 10,000 fps using optical fiber illumination. Opt. Express. Oct. 25, 2010;18(22):22722-33, doi: 10.1364/OE.18.022722.
Pfitzner et al., Rigid DNA beams for high-resolution single-molecule mechanics. Angew Chem Int Ed Engl. Jul. 22, 2013;52(30):7766-71. doi: 10.1002/anie.201302727. Epub Jun. 21, 2013.
Pinheiro et al., Challenges and opportunities for structural DNA nanotechnology. Nat Nanotechnol. Dec. 2011;6:763-72.
Plesa et al., Ionic permeability and mechanical properties of DNA origami nanoplates on solid-state nanopores. ACS Nano. Jan. 28, 2014;8(1):35-43, doi: 10.1021/nn405045x., Epub Dec. 5, 2013.
Ribeck et al., Multiplexed single-molecule measurements with magnetic tweezers. Rev Sci Instrum. Sep. 2008;79(9):094301.
Rief et al., Reversible unfolding of individual titin immunoglobulin domains by AFM. Science. May 16, 1997;276(5315):1109-12.
Rief et al., Sequence-dependent mechanics of single DNA molecules. Nat Struct Biol. Apr. 1999;6(4):346-9.

(56) References Cited

OTHER PUBLICATIONS

Rief et al., Single molecule force spectroscopy of spectrin repeats: low unfolding forces in helix bundles. J Mol Biol. Feb. 19, 1999;286(2):553-61.
Ritort, Single-molecule experiments in biological physics: methods and applications. J Phys Condens Matter. Aug. 16, 2006;18(32):R531-83. doi:10.1088/0953-8984/18/32/R01. Epub Jul. 25, 2006.
Robison et al., High-throughput single-molecule studies of protein-DNA interactions. FEBS Lett. Oct. 1, 2014;588(19):3539-46. Epub May 21, 2014.
Salazar-Banda et al., Determination of the adhesion force between particles and a flat surface, using centrifuge technique. Powder Technology. Apr. 2007;173(2):107-17.
Schmied et al., DNA origami-based standards for quantitative fluorescence microscopy. Nat. Protocols 9, 1367-1391 (2014).
Sitters et al. Acoustic force spectroscopy. Nature Methods 12, 47-50 (2015).
Tarsa et al., Detecting force-induced molecular transitions with fluorescence resonant energy transfer. Angew Chem Int Ed Engl. 2007;46(12):1999-2001.
Tzul et al., Modulation of folding energy landscape by charge-charge interactions: Linking experiments with computational modeling. Proc Natl Acad Sci U S A. Jan. 20, 2015;112(3):E259-66.
Van Oijen et al., Single-molecule kinetics of lambda exonuclease reveal base dependence and dynamic disorder. Science. Aug. 29, 2003;301(5637):1235-8.
Vargas et al., A centrifuge for studies of fluid dynamics phenomena in a rotating frame of reference. Revista Mexicana de Fisica. Jun. 2002;48(3):255-266.
Wagenbauer et al., Quantifying quality in DNA self-assembly. Nat Commun. Apr. 22, 2014; 5:3691, doi: 10.1038/ncomms4691, 7 pages.
Webster et al., Probing biomechanical properties with a centrifugal force quartz crystal microbalance. Nat Commun. Oct. 21, 2014;5:5284. 8 pages. doi: 10.1038/ncomms6284.
Williams et al., Entropy and heat capacity of DNA melting from temperature dependence of single molecule stretching. Biophys J. Apr. 2001;80(4):1932-9.
Wong et al., Exploring reaction pathways of single-molecule interactions through the manipulation and tracking of a potential-confined microsphere in three dimensions. Mat Res Soc Symp Proc. 2004. vol. 790: P5.1.1-5.1.12, Cambridge Univ. Press, Symposium held Dec. 1-4, 2003, Boston, MA, USA.
Wong et al., The effect of integration time on fluctuation measurements: calibrating an optical trap in the presence of motion blur. Optics Express. Dec. 11, 2006;14(25):12517-31.
Wong, Exploring single-molecule interactions through 3D optical trapping and tracking: from thermal noise to protein refolding. PhD Thesis, Dept. of Physics, Harvard University, Oct. 2006, 136 pages.
Woodside et al., Nanomechanical measurements of the sequence-dependent folding landscapes of single nucleic acid hairpins. Proc Natl Acad Sci U S A. Apr. 18, 2006;103(16):6190-5. Epub Apr. 10, 2006.
Yang et al., Multiplexed single-molecule force spectroscopy using a centrifuge. Nat Commun. Mar. 17, 2016;7:11026(1-7).
Yurke et al., Using DNA to power nanostructures. Genetic Programming and Evolvable Machines. 2003;4:111-22.
Zhang et al., Control of DNA strand displacement kinetics using toehold exchange. J Am Chem Soc. 2009;131(47):17303-14.
Zhang et al., Mechanoenzymatic cleavage of the ultralarge vascular protein, von Willebrand Factor. Science. Jun. 5, 2009;324(5932):1330-4.
Zhang et al., Optimizing the specificity of nucleic acid hybridization. Nat Chem 4, 208-214 (2012).
U.S. Appl. No. 15/862,947, filed Jan. 5, 2018, Published, 2018-0306783.
PCT/US2009/066154, Jul. 27, 2010, International Search Report and Written Opinion.
PCT/US2009/066154, Jun. 16, 2011, International Preliminary Report on Patentability.
EP 11728725.0, Jun. 16, 2016, European Examination Report.
PCT/US2011/038716, Aug. 29, 2011, International Search Report and Written Opinion.
PCT/US2011/038716, Dec. 4, 2012, International Preliminary Report on Patentability.
EP 15783027.4, Nov. 10, 2017, Extended European Search Report.
EP 19195115.1, Nov. 8, 2019, Extended European Search Report.
PCT/US2015/027290, Aug. 13, 2015, Invitation to Pay Additional Fees.
PCT/US2015/027290, Oct. 28, 2015, International Search Report and Written Opinion.
PCT/US2015/027290, Nov. 3, 2016, International Preliminary Report on Patentability.
PCT/US2016/065341, Jan. 30, 2017, Invitation to Pay Additional Fees.
PCT/US2016/065341, Apr. 12, 2017, International Search Report and Written Opinion.
PCT/US2016/065341, Jun. 21, 2018, International Preliminary Report on Patentability.
EP 17757284.9, Dec. 6, 2019, Supplementary Partial European Search Report.
PCT/US2017/019318, Jun. 7, 2017, International Search Report and Written Opinion.
PCT/US2017/019318, Sep. 7, 2018, International Preliminary Report on Pentability.

* cited by examiner 29 bp DNA INTERACTION

LOOPED

UNLOOPED

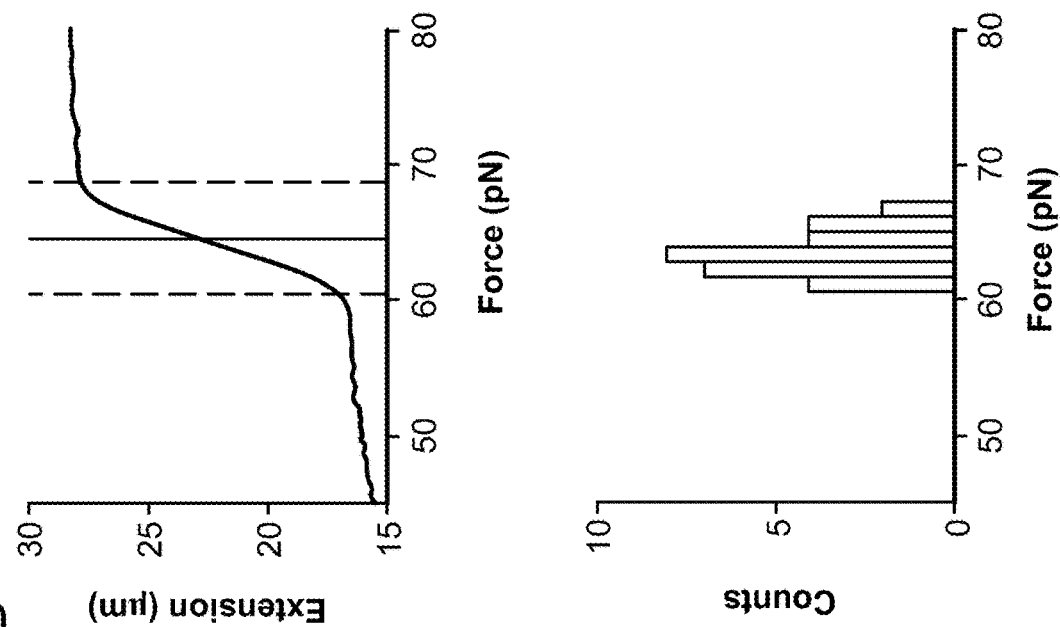
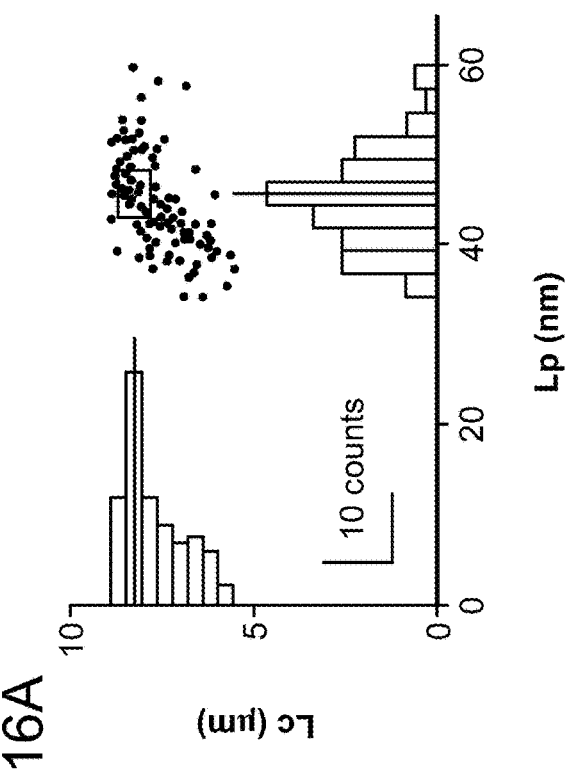
FIG. 16A
FIG. 16B

SEQUENCE LISTING

```
<160> NUMBER OF SEQ ID NOS: 2

<210> SEQ ID NO 1
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 1
cacgaattct ctgcctccct tttaaccta g                              31

<210> SEQ ID NO 2
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 2
ctcaaatatc aaaccctcaa tcaatatct                                29
```

SPINNING APPARATUS FOR MEASUREMENT OF CHARACTERISTICS RELATING TO MOLECULES

CROSS-REFERENCE TO RELATED APPLICATIONS

This application is a national stage filing under 35 U.S.C. 371 of International Application PCT/US2017/019318, filed Feb. 24, 2017, which was published under PCT Article 21(2) in English, and which claims the benefit of U.S. Provisional Application No. 62/299,711, entitled "SPINNING APPARATUS FOR MEASUREMENT OF CHARACTERISTICS RELATING TO MOLECULES," filed on Feb. 25, 2016. These applications are incorporated herein by reference.

FEDERALLY SPONSORED RESEARCH

This invention was made with U.S. Government support under grant number 2011080983 awarded by the National Science Foundation and grant number 1R21GM107907-01A1 awarded by the National Institutes of Health. The Government has certain rights in the invention.

BACKGROUND

1. Field

Aspects described herein relate generally to a spinning apparatus for measurement of characteristics relating to molecules, and methods of measuring such characteristics.

2. Discussion of Related Art

The ability to quantify interactions between biomolecules is of great interest for scientific and medical research, as well as for drug development. Examples of measurable characteristics of a biomolecular interaction include the affinity (e.g., how strongly the molecules bind/interact) and the kinetics (e.g., rates at which the association and dissociation of molecules occur) of the interaction. Traditionally, such characteristics are measured in solution, using methods such as calorimetry, stop-flow imaging, or surface plasmon resonance. These bulk measurements are limited in many ways, including 1) they report only average behavior and thus may lose important details associated with metastable states and rare events, and 2) they measure chemistry in the absence of externally applied mechanical stress, which can be dramatically different from crowded and dynamic environments in living systems.

Force probes that apply single molecule measurement methods include atomic force microscopes (AFM), optical traps, magnetic tweezers, biomembrane force probes, and flow chambers. Due to technical complexities, some systems require a large investment of money and time (e.g. optical trap systems typically cost $150,000 or more). Additionally, molecular interactions are studied one molecule at a time in most cases. Statistical characterization of these interactions is therefore slow and painstaking, requiring hundreds or thousands of measurements which are typically performed in a serial manner.

SUMMARY

In an illustrative embodiment, an apparatus for measuring a characteristic of a sample device is provided. The apparatus includes a module, which includes a sample holder, a light source configured to illuminate the sample, and a detector configured to receive light from the sample. The module is sized and dimensioned to fit within a centrifuge receptacle having a volume of less than or equal to 1 L.

In another illustrative embodiment, a method includes attaching a particle to a surface through a molecular interaction associated with a first molecule and a second molecule. The method also includes rotating the surface about an axis of rotation to apply a centrifugal force to the particle, the centrifugal force having a direction. The method further includes hitting the particle with light from a light source and detecting an image of the particle with a detector during rotation of the surface, the image containing information representing a characteristic of the molecular interaction. The method also includes determining the characteristic of the molecular interaction based on the detected image. An imaging axis is angled relative to direction of centrifugal force, the imaging axis being oriented along the direction at which light from the light source hits the sample.

In yet another illustrative embodiment, a method includes attaching a DNA nanoswitch to a surface and rotating the surface a first time to apply a force to the particle. After rotating the surface the first time, the method includes stopping rotation of the surface. After stopping rotation of the surface, the method further includes rotating the surface a second time to apply a force to the particle. The method also includes detecting images of the particle with a detector during rotation of the surface the first time and the second time, the images containing information representing a characteristic of the molecular interaction. The method further includes determining the characteristic of the molecular interaction based on the detected images.

In yet a further illustrative embodiment, a method includes attaching a particle to a surface through a molecular interaction associated with a first molecule and a second molecule. The method also includes inserting the surface into a centrifuge and selecting a centrifuge temperature using a temperature control built into the centrifuge. The method further includes rotating the surface a first time to apply a force to the particle and detecting an image of the particle with a detector during rotation of the surface, the image containing information representing a characteristic of the molecular interaction. The method also includes determining the characteristic of the molecular interaction based on the detected image.

Various embodiments provide certain advantages. Not all embodiments of the present disclosure share the same advantages and those that do may not share them under all circumstances.

Further features and advantages of the present disclosure, as well as the structure of various embodiments are described in detail below with reference to the accompanying drawings.

BRIEF DESCRIPTION OF THE DRAWINGS

Various embodiments will now be described, by way of example, with reference to the accompanying drawings, in which:

FIG. 16 depicts graphs associated with parallel DNA force-extension and overstretching measurements made with a spinning force system;

DETAILED DESCRIPTION

Figure 1B:
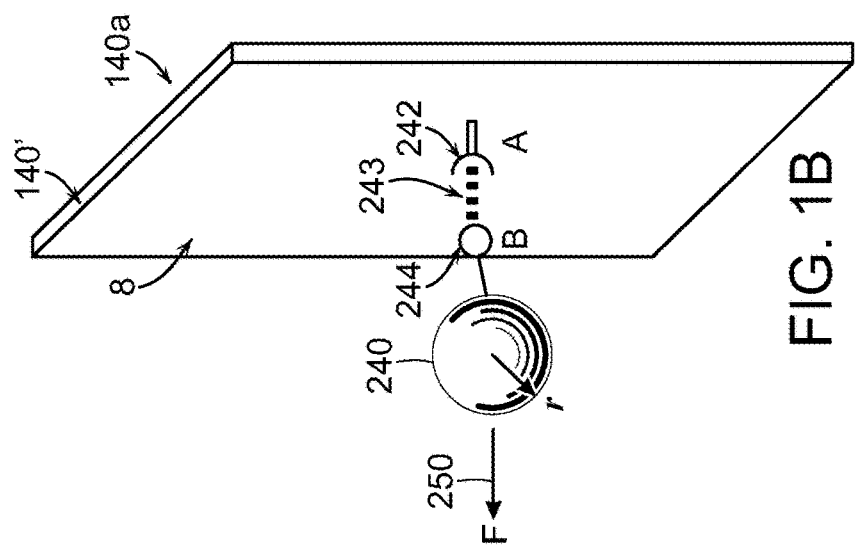
FIG. 1B depicts a centrifugal force applied to the sample of FIG. 1A.

The system and methods of operation discussed herein can provide massively-parallel high-throughput single-molecule force measurements at a low cost. More specifically, rotation-induced forces (e.g., centrifugal forces and viscous drag forces) can be used to manipulate events such as single molecules (e.g., proteins or DNAs), single molecular interactions or molecular complexes (e.g., receptor-ligand protein pairs), enabling forces to be applied to many events simultaneously and/or repeatedly. Each event (also referred to herein as a subject) can be observed directly and independently for true single-molecule detection. The efficiency of experiments can be improved, reducing the time to conduct an experiment from days to minutes. More than simply speeding up experiments, this efficiency also enables new experiments such as near equilibrium measurements that observe interactions with hour-long lifetimes, which would be unfeasible with sequentially collected statistics. Furthermore, with larger statistical sets more easily attainable, more detailed characterizations, model testing, and observations of population heterogeneity are possible. Parallel measurements can also be used to test families of interactions simultaneously (e.g., multiple drug candidates could be tested simultaneously against a target receptor).

The system and methods of operation discussed herein can provide accurate force control in a wide range of directions and magnitudes. Through force control, the system and methods of operation can be used to quantify force dependent interactions, including measuring the force dependence of kinetic parameters (e.g., $K_{on}$ and $K_{off}$) and molecular subtleties which would be invisible from population averaging. Using this system, the mechanical properties of biomolecular complexes (e.g., compliances of DNAs and proteins) and cellular targets (e.g., elasticity of stress-bearing cells) can be studied, yielding valuable information into both the structure and the function of those subjects.

The centrifugal force field applied to a sample in some embodiments of the system and methods of operation described herein is macroscopically uniform, stable without the need for active feedback, calibration-free, and dynamically controllable in an essentially deterministic way. Thus, a desired force history can be applied to an ensemble (or plurality) of single molecules or events (whether identical or different from each other) without the need for active feedback. The force field conveniently couples to mass density, eliminating the possibility of radiative damage and expanding the range of systems that can be studied with force (e.g., beads or objects made of any material can be used, as long as they have a different mass density than their surroundings). Furthermore, by varying the bead type, bead size, and rotation speed, a wide range of forces, at least from sub-femtoNewtons to nanoNewtons, can be achieved.

The system and methods of operation described herein can be conveniently integrated with various types of force probes to generate forces in multiple dimensions with high flexibility. For example, the system can be used in conjunction with optical traps, magnetic tweezers and/or microfluidic devices to generate a combination of forces (such as gradient and scattering forces, magnetic forces, hydrodynamic forces, and centrifugal forces). Each force can be applied to a sample (or event) in a different direction, with a different magnitude, and/or at a different test stage.

The system and methods of operation described herein can also be conveniently integrated with various imaging techniques to provide real-time observation with high temporal and spatial resolution. For example, using interference techniques and diffraction analysis, the position of individual particles in a sample can be ascertained with sub-nanometer accuracy. Also, fluorescent imaging can be used to enable visualization of subtle molecular transitions during experiments. Moreover, using video tracking by high-speed CCD cameras, molecular events can be detected on the scale of microseconds.

In some embodiments, the systems and methods described herein can be more cost effective and simpler to use than other common methods of molecular spectroscopy. The material cost of a module described herein is generally less than the cost of a typical laboratory microscope. In some embodiments, experiments using this system are straightforward, with a pre-preprogrammed force protocol, minimal setup, and little or no need for user intervention.

The inventors have appreciated that the ability to mechanically manipulate single molecules or molecular interactions can lead to insights throughout biomedical research, from the action of molecular motors in replication and transcription to the role of mechanical forces in development. The inventors have recognized that, while in principle these approaches enable the full characterization of individual molecular complexes and the study of population heterogeneity at the single-molecule level, in practice, key challenges exist. The first challenge for force spectroscopy studies is the low throughput of most single-molecule approaches. Furthermore, sufficient statistics must be collected not only for the population, but also for each individual molecule or interaction or complex, which can be a challenge for studying catastrophic transitions such as bond rupture. Another challenge is the positive identification of the single-molecule interactions of interest over non-specific and multiple interactions. Finally, there is the subtle challenge of noise, both thermal and experimental, that makes distinguishing different populations of molecules with similar force properties difficult.

The inventors have addressed these challenges with spatiotemporally multiplexed force spectroscopy. In some embodiments, the system can accomplish parallel spatial multiplexing with repeated interrogation. In some embodiments, repeated interrogation is enabled by self-assembled nanoscale devices. The inventors have developed a spinning force system for high-throughput single-molecule (or single interaction) experimentation that, in some embodiments, utilizes a commercial benchtop centrifuge.

In the spinning force system, an entire microscope imaging system is rotated to observe microscopic objects subjected to uniform centrifugal force (unlike earlier "spinning disk" centrifuge microscopes[19, 20]). This design enables, in some embodiments, temperature control and high-resolution particle tracking (~2 nm). As an illustrative embodiment and application, the inventors have developed a high-throughput assay that integrates mechanical nanoswitches, such as those described in published PCT application WO2013/067489 (the entire contents of which are incorporated herein) to provide important new functionality. The nanoswitches can serve two roles—one as a molecular signature to facilitate reliable and automated analysis of large data sets, and the second to enable the repeated interrogation of each single-molecule pair (or single molecular interaction), increasing throughput and enabling new measurements of heterogeneity in single-molecule (or single molecular interaction) experiments. By making repeated force measurements on hundreds of single-molecule complexes (such as single nanoswitches that, as described below, may embrace both members of a binding pair), multiple statistics on each molecule (or nanoswitch, and thus each interaction of interest) that comprises the population can be collected. The inventors have also recognized that by averaging multiple rupture forces on a per-molecule basis (e.g., per nanoswitch basis), noise can be reduced to enable super-resolved force spectroscopy—the identification of different populations of molecules (e.g., nanoswitches) below the thermal force-resolution limit. Averaging allows reduction of the spread in force distributions (averaging reduces noise by a factor of ~sqrt(N)) without losing information about differences between molecules (e.g., nanoswitches). Furthermore, the rich and relatively large data sets provided by this technique could also complement other analysis techniques for statistical deconvolution[22, 23].

Schematic Overview

Figure 1A:
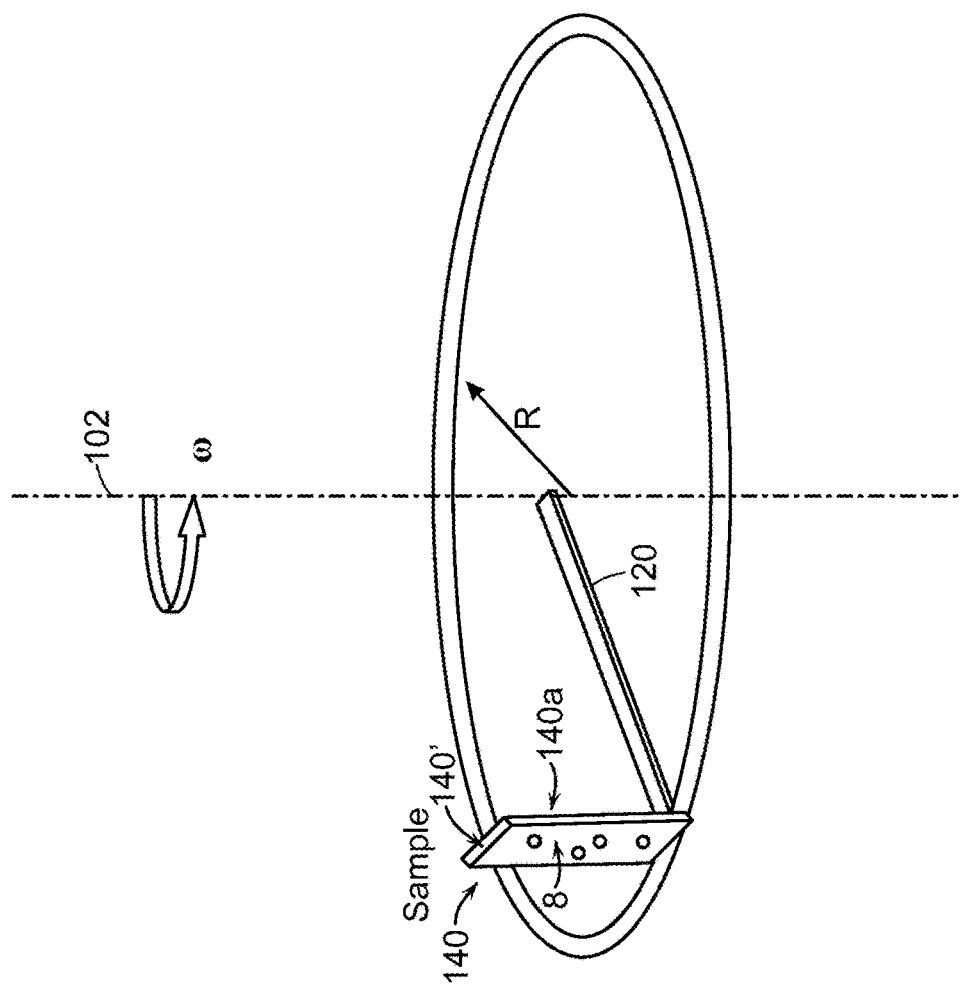
FIG. 1A depicts a simplified schematic representation of an apparatus for measuring a characteristic of a sample.

Referring to FIGS. 1A and 1B, when rotary arm 120 is in operation, sample 140 rotates at an angular velocity ω and at a distance R from the center of axis 102. For illustrative purposes, in this example, sample 140 includes a cover slip 140' having an inner surface 140a and an outer surface 8 with respect to axis 102. Both surfaces are aligned in parallel with axis 102. A particle 240 (e.g., a bead) adheres to outer surface 8 through a chemical bond 243 formed between molecule A 242 and molecule B 244. In this example, molecule A is a receptor chemically linked to outer surface 8, and molecule B is a ligand chemically linked to particle 240. (The techniques and methods for forming such linkages will be described in greater detail below).

When particle 240 undergoes circular motion, a centrifugal force F is exerted on the particle, as defined by the following equation:

$$F = \frac{mv^2}{R} \quad (1)$$

where F is the net centrifugal force, m and v are the mass and the linear velocity of the particle, respectively, and R is the distance of the particle from rotation axis 102. In a rotating reference frame in which orbiting particle 240 appears stationary, particle 240 experiences an inertial centrifugal force equal to F in a direction perpendicular to outer surface 140b and away from central axis 102 (shown by arrow 250). In some examples where particle 240 is a spherical bead in solution with radius r and relative density ρ, rewriting equation (1) in terms of angular velocity ω yields:

$$F = \frac{4\pi\rho r^3 R\omega^2}{3} \quad (2)$$

When sample 140 rotates about axis 102 at a very low speed, centrifugal force F is countered by the interaction force of chemical bond 243, allowing particle 240 to continue to adhere to surface 8. As the angular velocity ω rises, the increasing magnitude of centrifugal force F causes bead 240 to move with respect to surface 8. The characteristics of the relative motion (e.g., the root-mean-square displacement or the direction of the motion) can be monitored and analyzed to quantify certain chemical and/or mechanical properties of bond 243 (e.g., properties associated with its transitional states and conformational changes). The increasing F may also cause the rupture of chemical bond 243, at which point, particle 240 is released from surface 8. The magnitude of centrifugal force F at the particle release indicates the rupture force of chemical bond 243.

During operation, the magnitude of centrifugal force F can be controlled, for example, by adjusting the angular velocity ω of rotary arm 120. For instance, sample 140 can be subjected to multiple cycles of force application in which the centrifugal force on particle 240 is increased and/or decreased through step changes in angular velocity ω.

In addition to changing the angular velocity ω, it is also possible to change the radius of rotation R either statically or dynamically by changing the sample position relative to the axis of rotation. For example, in system 100, sample 140 may be mounted to an adjustable rotary arm with extendible length, or staged on a positioner that can be translated in a radial direction with respect to central axis 102.

In embodiments where particle 240 is a spherical bead, the centrifugal force F can also be varied by changing one or more of the particle characteristics ρ and r shown in equation (2). For example, microspheres are commercially available in a wide range of materials and sizes (see Table 1 below). By conjugating subjects of study (e.g., molecules, proteins, nucleic acids, cells, etc.) to selected beads, such as microspheres, the centrifugal force applied to the beads (and translated to the subject) can be varied based on bead properties. In addition, the degree of monodispersity of beads can control the range of forces applied for a given spin. For instance, a highly monodisperse sample (e.g., using beads of substantially the same size and properties) may cause all beads to experience the same force, while a polydisperse sample (e.g., using beads of various sizes and/or properties) would have a wide range of forces being applied. Moreover, ρ of particle 240 can also be altered by changing the density of the buffer solution. Furthermore, the geometry of the sample chamber can be varied to control the effects of fluid flow, which can add hydrodynamic forces to immobilized particles in the chamber.

TABLE 1

Materials and sizes of beads

| Bead Material | Specific Density (g/cm$^3$) | Size Range (μm) |
|---|---|---|
| Borosilicate | 1.5 | 1-100+ |
| Polystyrene | 0.05 | 0.05-100+ |
| Silica | 1.2 | 0.01-100 |
| Gold | 18.3 | 0.002-0.25 |
| Melamine | 0.51 | 0.5-10 |
| Iron Oxide | 4.24 | 10-Jan |

With proper parameter selection, the force applied to particle 240 can span 9 orders of magnitude, ranging from microNewtons (e.g., r=10 μm, ρ=1.5 g/cm$^3$, R=500 mm, ω=100 Hz) to femtoNewtons (e.g., r=1 μm, ρ=0.05 g/cm$^3$, R=250 mm, ω=2 Hz).

The direction of the centrifugal force F can also be controlled. In some examples, sample 140 may be coupled to a surface 8 (e.g., of a cover glass, other coverslip or other sample chamber or sample mounting element) that is perpendicular to rotational axis 102, resulting in a centrifugal force F along surface 8. In some embodiments, sample 140 may be coupled to an outer surface 8 (i.e., a surface facing away from the rotational axis 102) that is parallel to rotational axis 102, resulting in a tensile force on the bond 243, as shown in FIG. 1B. For particular implementations, it may be desirable to couple a sample to a surface that is parallel to rotation axis 102 because pulling particle 240 away from surface 8 reduces the likelihood of the particle forming new interactions with unoccupied binding sites of molecule A on the surface 8. In some embodiments, a compressive (rather than tensile) force can be applied to bond 240 if the sample is coupled to an inner surface 140a (i.e., a surface facing toward the rotational axis 102).

In some embodiments, sample may be coupled to a surface that forms a selected angle with respect to rotational axis 102 so that centrifugal force F may be applied in any given direction. In some implementations, it may be desirable to couple sample to a surface that is at an oblique angle with respect to the rotation axis 102. As will be discussed in a later section, this oblique angle arrangement may allow one to track lateral particle motion—i.e., motion of the particles occurring parallel to the surface to which the sample is coupled.

In addition to centrifugal force F, other types of forces can also be applied to particle 240 through spinning. For example, if particle 240 is contained in a chamber filled with a liquid medium, the rotation of sample 140 can generate regional flows that exert a viscous drag force to particle 240. The direction of the drag force depends on factors such as the geometry of the chamber and the orientation of the sample. The magnitude of the drag force depends on factors such as the viscosity and the temperature of the liquid medium, the size of the particle, and the angular velocity and acceleration of the sample.

In the apparatus for measuring a characteristic of a sample (such as a molecule such as a nanoswitch), motion of particle 240 (e.g., displacement caused by molecular folding, unfolding or rupture of bond 243) can be observed by video tracking methods (e.g., by taking successive images of the particle at a high temporal resolution). As will be discussed, a light source, sample and objective may rotate together at the same angular velocity ω, and thus these three components appear stationary to each other in a rotating reference frame. Therefore, images of particle 240 can be formed using traditional imaging techniques, including transmitted- or reflected-light techniques and fluorescence techniques.

System Overview

According to one aspect, in some embodiments, the apparatus for measuring a characteristic of a sample is a small-scale spinning force system that uses a centrifuge that is standard equipment in scientific laboratories. In some embodiments, the centrifuge is a benchtop centrifuge, such as the Thermo Scientific Heraeus X1R Centrifuge. The use of standard equipment can decrease the cost and increase the accessibility of the spinning force approach to molecular characterization.

The spinning force system also includes a module that, in some embodiments, holds the optical components and the sample being investigated. The module can be sized and shaped to fit within the centrifuge, e.g., within a bucket of the centrifuge or within the holes or slots of the centrifuge. In some embodiments, the module is sized and shaped to fit within a 400 mL bucket volume or less. In some embodiments, the module is smaller, and is sized and shaped to fit within a 15 mL, 50 mL or less, 100 mL or less or 1 L or less tube/bucket/volume.

Figure 2:
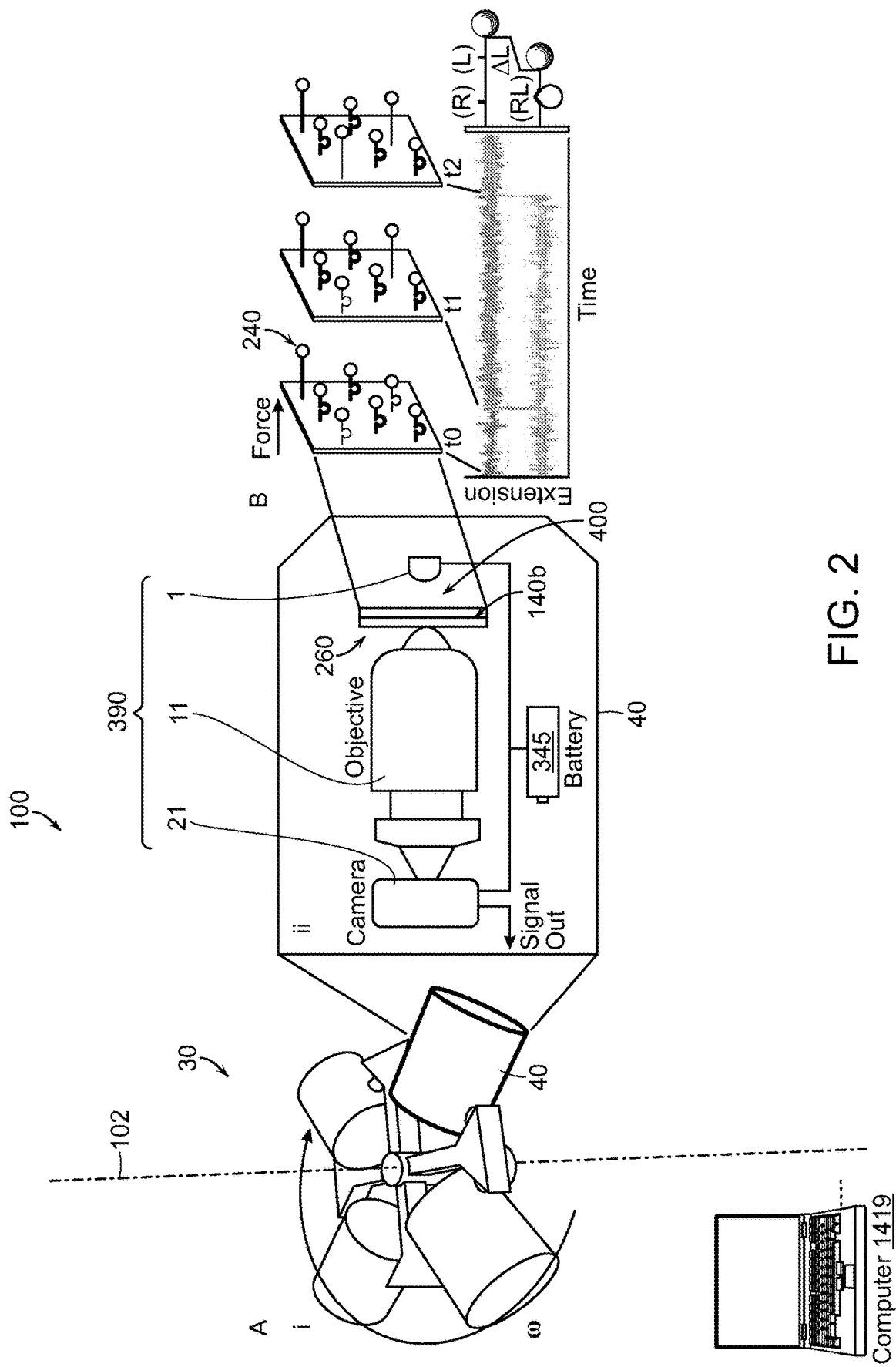
FIG. 2 depicts a schematic of one embodiment of an apparatus for measuring a characteristic of a sample.

Referring to panel A of FIG. 2, a spinning force system 100 uses a standard laboratory centrifuge 30 to provide rotational force for the study of molecular interactions. In some embodiments, the module 300 that holds the optical components 390 and the sample 400 may be sized to fit within one of the swing buckets 40 of the centrifuge. The optical components 390 may include a detector 21, an objective 11, and a light source 22. A battery 345 for powering the optical components and/or a media converter may be included inside the centrifuge bucket 40. The spinning force system 100 may include a computer 1419 that receives signals from the detector 21. In some embodiments, signals from the detector 21 are first sent to a media converter, which then sends signals to a computer 1419. In some embodiments, the computer 1419 or other controller may be arranged to control the centrifuge, e.g., control angular velocity, angle of the bucket, rotation duration, start and stop times, etc. The centrifuge may use a control module that enables control by a computer or other controller.

The module's sample holder may be a chamber, slot or other space or attachment point in the module into which sample or something holding the sample can be inserted or otherwise attached to. For example, as will be discussed in more detail below, in some embodiments, a sample chamber 260 comprises two glass surfaces adhered together (e.g. at their borders), while leaving a gap between the coverslips within the borders to accommodate sample. Sample, such as a population of nanoswitches, is coupled to one of the surfaces and portions of the sample are permitted to move toward or away from the surface it is coupled to in response to an application of centrifugal force from the centrifuge. The sample chamber can then be inserted into the module's sample holder, which may be a slot or space into which the sample chamber may be snapped into, slid into, or otherwise coupled to. In some embodiments, the surface to which the sample is coupled to (e.g., the cover glass or other coverslip) may be disposable.

A variety of different types of samples may be held by the sample holder. In some embodiments, the sample includes nanoswitches, such as DNA nanoswitches. Panel B of FIG. 2 depicts a magnified view of the sample 400 that is coupled to a surface 8 of a sample chamber 260, which is in turn held by a sample holder of a module (an example of a sample holder is shown as item 340 in FIGS. 5 and 7). In some embodiments, the sample may be directly coupled to the sample holder of the module, such that no sample chamber is needed.

The sample 400 in FIG. 2 includes a plurality of nanoswitches such as DNA nanoswitches. The images corresponding to t0, t1, and t2 depict the configuration of the nanoswitches over time, as the applied force is increased over time, e.g. due to increased angular velocity of the centrifuge. The graph at the lower portion of panel b reflects tether extension monitored as a function of time when force is applied. Molecular transitions such as a bond rupture between a receptor (R)—ligand (L) pair, the pair being part of the nanoswitch, causes a well-defined change in tether extension of the nanoswitch, providing a distinct signature for detecting interactions between two molecules of interest, both of which may be integral to the nanoswitch.

Thus, the methods and devices can be used to measure interaction strength or other parameter relating to two separable and physically distinct binding partners that are bound to each other and then are separated from each other via a bond rupture. One such binding partner is conjugated to a detectable moiety such as a particle and it is the location of the detectable moiety that denotes information about the state of the bond between the two binding partners.

In the case of a nanoswitch, both binding partners are conjugated to or are part of the same molecule (such as for example a nucleic acid), referred to herein as the nanoswitch. The binding partners are spaced sufficiently apart from each other along the nanoswitch such that they are able to interact and bind to each other. The nanoswitch comprises a detectable moiety such as a particle, at or near its free end. Increasing the force on the nanoswitch, via the particle for example, will rupture the bond between the two binding partners, thereby causing the length of the nanoswitch to change (i.e., increase, typically), and in so doing the position of the particle also changes.

FIG. 2, panel B depicts some nanoswitches in an open or extended conformation and other nanoswitches in a closed or looped conformation. Those in the open or extended conformation have experienced a bond rupture, and this informs an end user that the force applied to nanoswitch is greater than the binding force (or energy) between the two binding partners. Conversely, those in the closed or looped conformation have not yet experienced a bond rupture, and this informs an end user that the force applied to the nanoswitch is less than the binding force (or energy) between the two binding partners.

The various nanoswitches on a support in a single run may be identical to each other or they may be different. Identical nanoswitches comprise the same backbone molecule and the same binding partners at the same positions along the backbone molecule (e.g., nucleic acid). Different nanoparticles may comprise different binding partners, optionally at different positions along the backbone molecule (e.g., nucleic acid). If at different positions, then different nanoswitches, and thus different binding pairs, may be identified based on the change in their length from a looped to an extended conformation.

The above description assumes that a nanoswitch comprises two binding partners and is used to study the binding characteristics of two binding partners to each other. However, it should be understood that this disclosure contemplates more complex nanoswitches that involve two or more binding pairs and/or three or more binding partners that interact and/or potentially compete for binding with each other.

Figure 3:
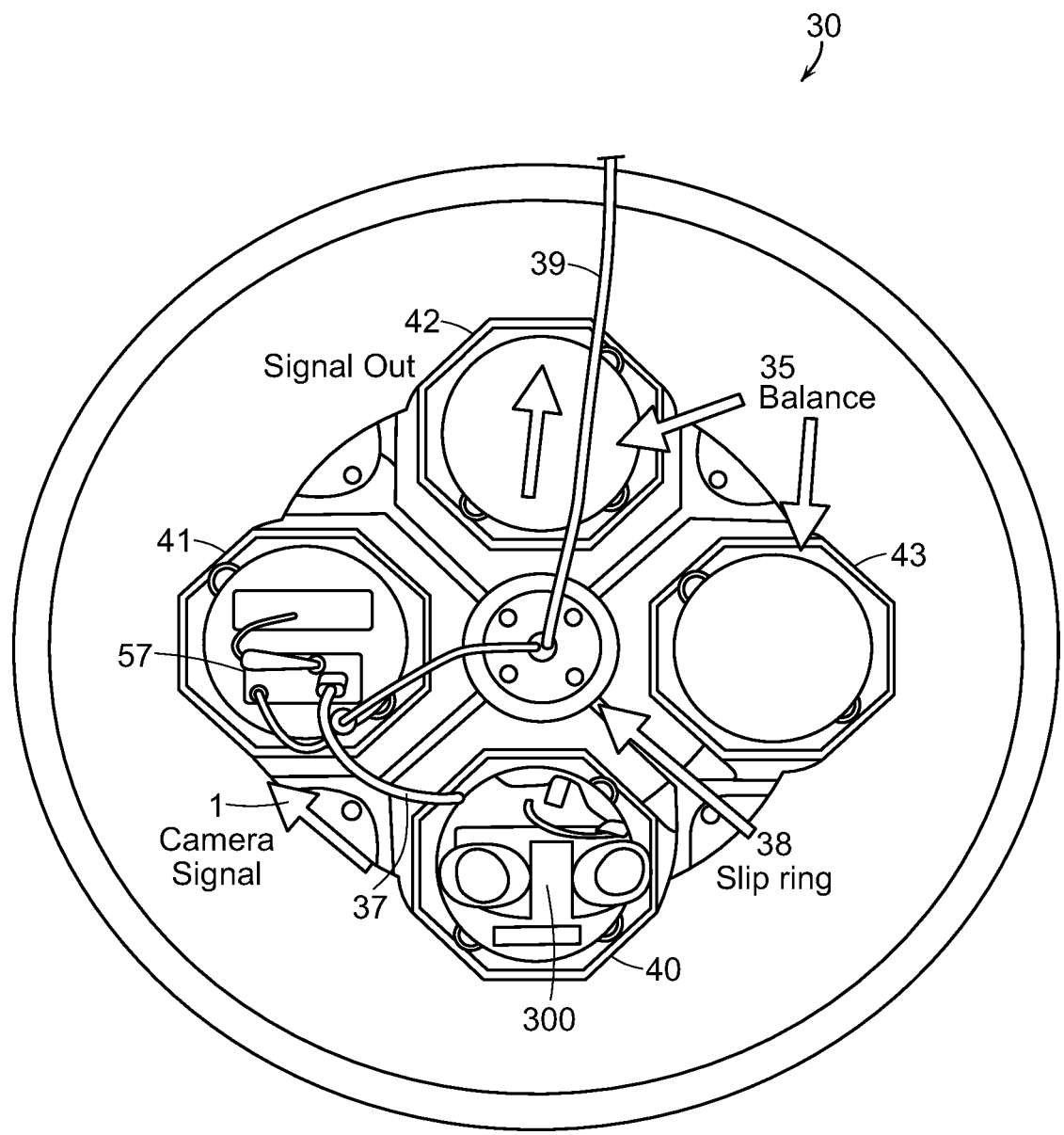
FIG. 3 depicts a top-down view into a centrifuge of a spinning force system.
Figure 4:
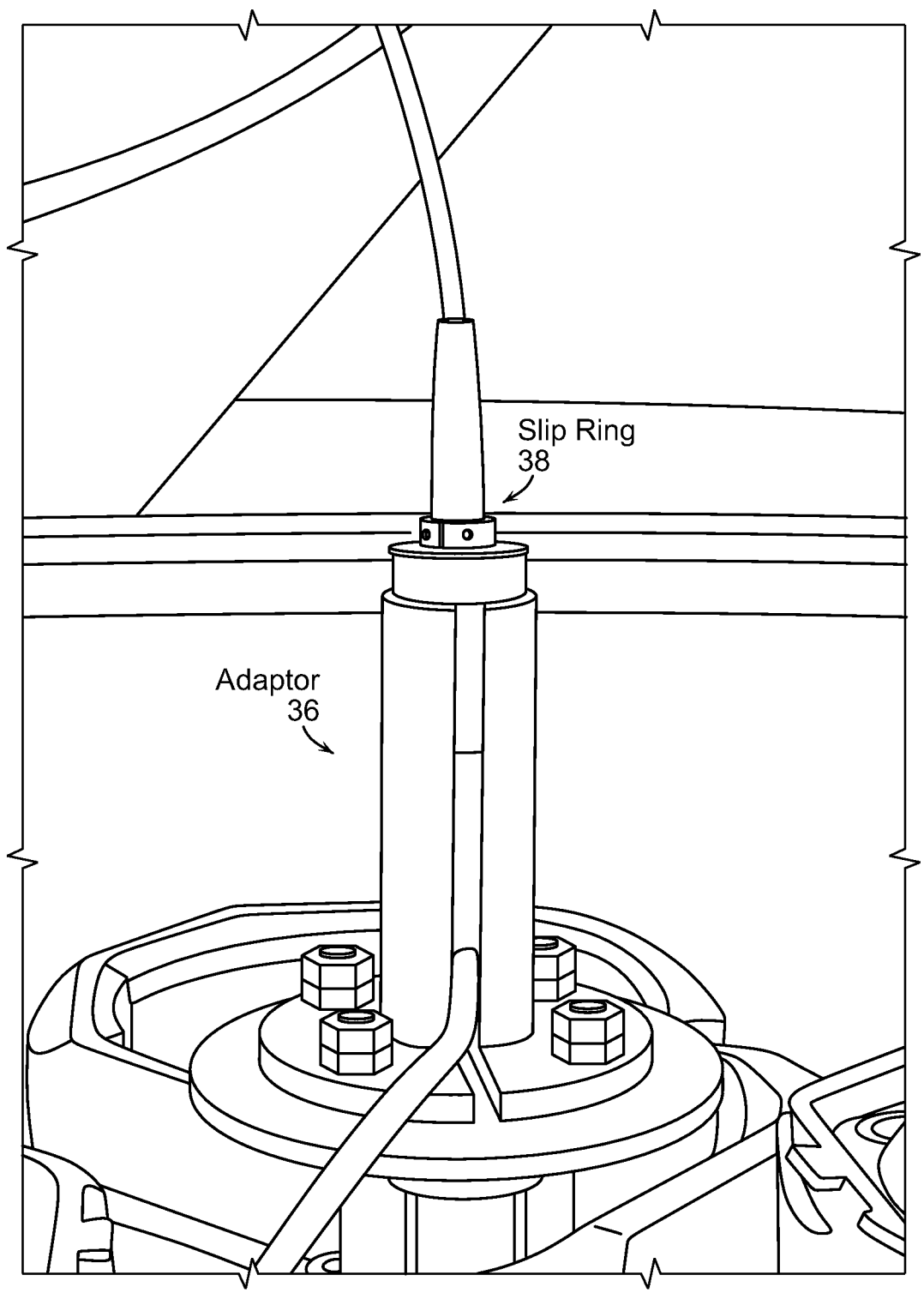
FIG. 4 depicts a detailed view of a slip ring of the centrifuge of FIG. 3 with a cable running through the slip ring.

One illustrative example of a spinning force system 100 is shown in FIG. 3, which depicts a top-down view into a centrifuge 30 having four buckets. The centrifuge may be a standard benchtop centrifuge that is commonly found in scientific laboratories (e.g., the Thermo Scientific Heraeus X1R Centrifuge). The first bucket 40 holds a module containing optical components and a sample. In some embodiments, transmission of camera data out of the centrifuge during centrifugation is accomplished by converting the camera's gigabit Ethernet signal to a fiber-optic signal, then passing this data out of the centrifuge through a fiber rotary joint. The adjacent bucket 41 holds electrical components for signal conversion. In one embodiment, the second bucket 41 includes a media converter 57 that converts camera signals from the module to a fiber optic signal. The bucket also includes a battery to power the media converter 57. A first cable 37 connects the module 300 to the media converter 57. In some embodiments, the media converter is part of the module. A second cable 39 is a fiber optic cable that sends a fiber optic signal from the media converter out to a computer or other device outside of the centrifuge. In some embodiments, the fiber optic cable may run through a slip ring 38 before exiting the centrifuge. FIG. 4 shows a detailed view of the slip ring 38 with the cable 39 running through it. As is well known in the art, the slip ring is an electromechanical device that allows the transmission of power and/or electrical signals from a stationary to a rotating structure. The slip ring 38 allows the portion of cable downstream of the slip ring (i.e. the portion of the cable exiting the centrifuge) to remain stationary while the centrifuge rotor and the cable upstream of the slip ring (i.e. the portion of cable running from the media converter to the slip ring) rotates.

In an embodiment using the Thermo Scientific Heraeus X1R Centrifuge, the TX-400 rotor can be modified to mount a fiber optic rotary joint (Princetel MJX) along the central axis. This can be accomplished by removing the rotor's central push-release mechanism (by loosening the screw on the side of the button), and threading the four existing through holes to accept 10-32 screws. An adapter can be installed on the rotor to hold the slip ring. In one illustrative example, FIG. 4 depicts an adaptor 36 that is installed to accommodate the slip ring 38. To enable the fiber optic cable to pass through the lid of the centrifuge, the central plastic viewing window of the centrifuge was removed.

It should be appreciated that, in some embodiments, the electrical components for converting signals may be incorporated into the module, or may be eliminated completely. For example, in some embodiments, the module may send signals wirelessly such that no conversion to a fiber optic signal is needed. Turning back to FIG. 3, the next two buckets 42, 43 hold balances 35 that balance out the weight of the first two buckets.

Figure 5:
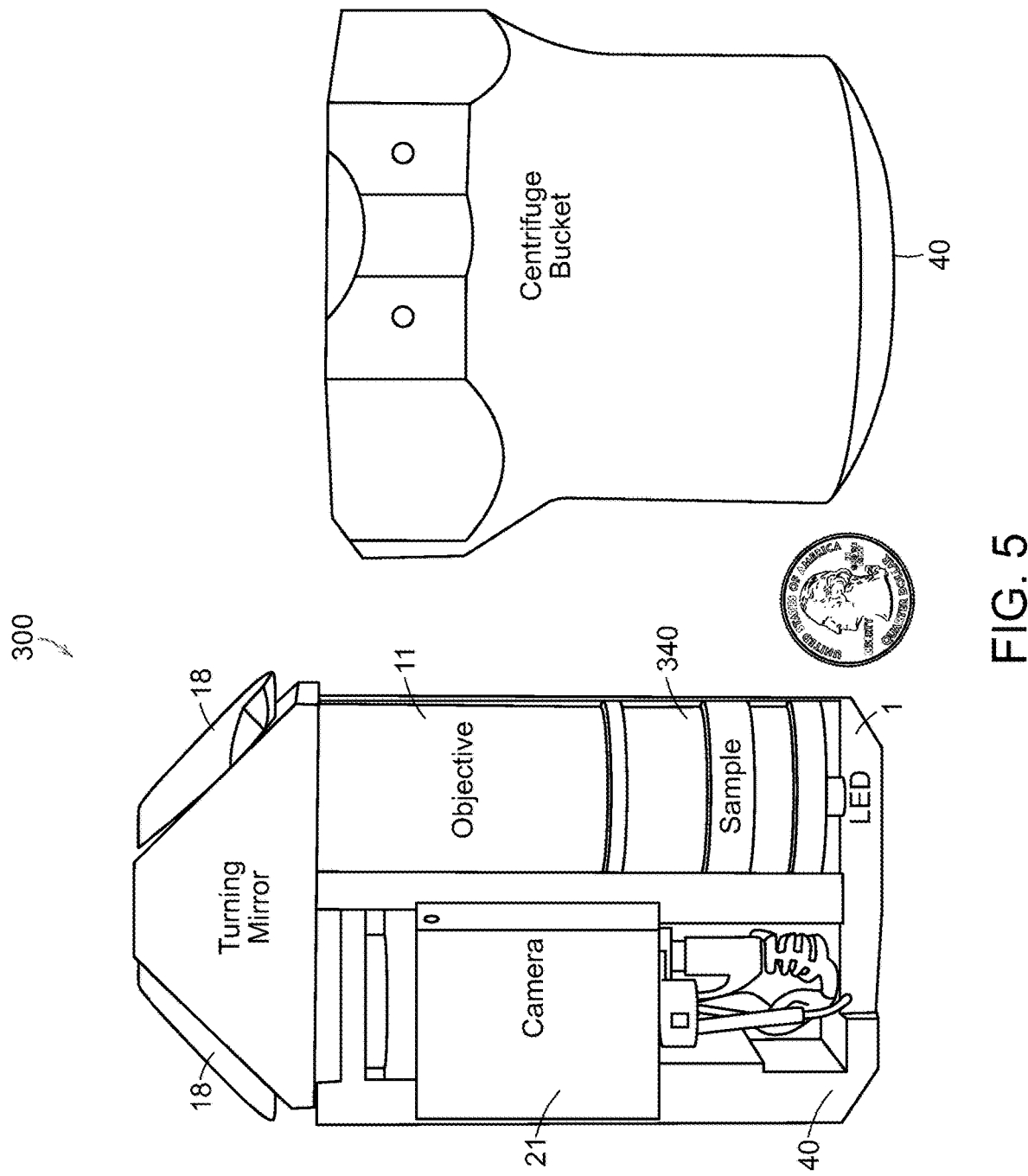
FIG. 5 depicts a cutaway view of a module held within a centrifuge bucket (left) and a centrifuge bucket with the module removed (left)

The module will be discussed in detail next. The left side of FIG. 5 shows that the module 300 is sized to fit within a centrifuge bucket 40. The right side of FIG. 5 shows the centrifuge bucket with the module removed. The module may hold optical components as well as the sample 400. The optical components of the module include a light source in the form of an LED, an objective, a detector 21 in the form of a camera, and a turning mirror that redirects light from the light source 22 to the camera. To allow the module to fit within a confined volume, in some embodiments, the optical path may include two right-angle bends. In the illustrative embodiment of FIG. 5, the turning mirrors 18 enable these two right-angle bends. As a result, some of the optical components may be placed side-by-side to one another rather than being placed in a straight line. In this manner, the overall length of the entire assembly is decreased, enabling the module to be compact enough to fit within the centrifuge bucket.

Figure 6:
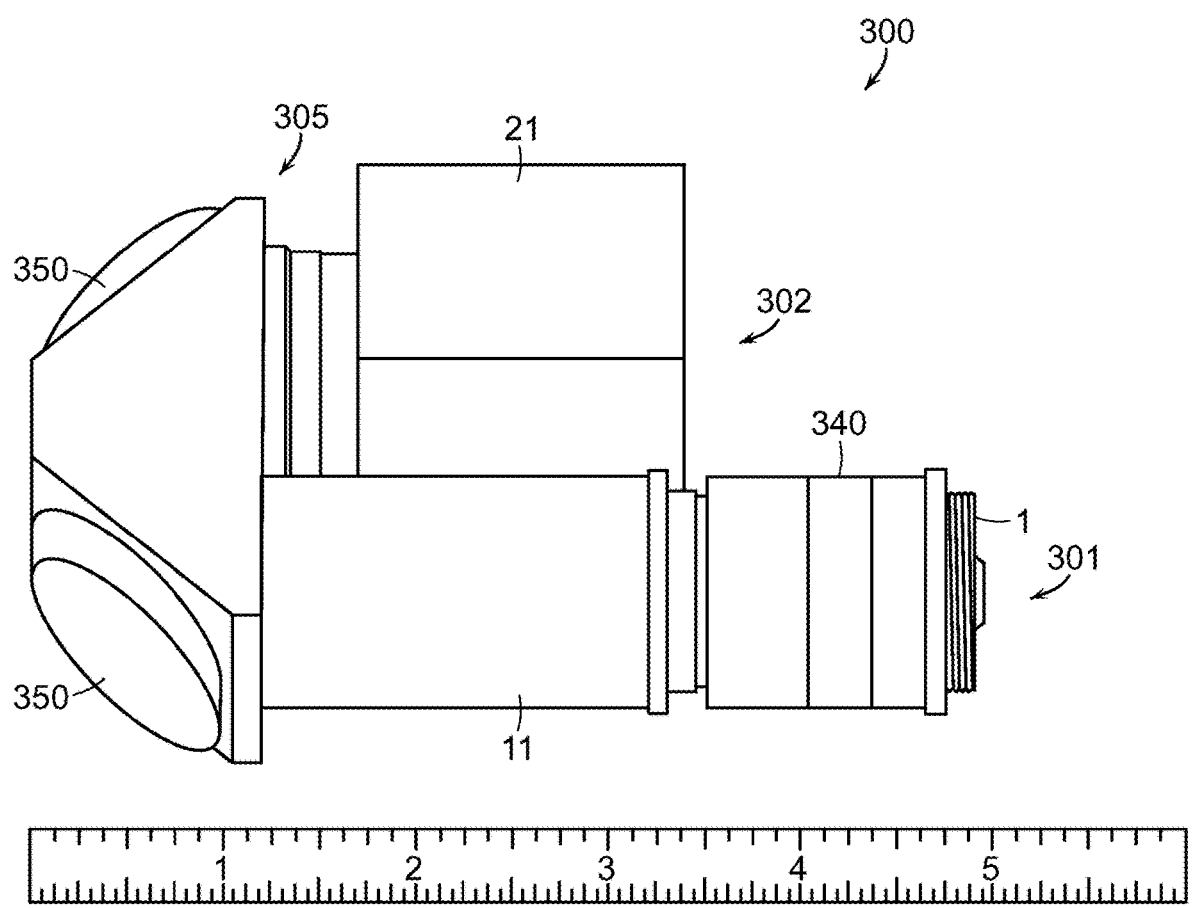
FIG. 6 depicts a perspective view of the module of FIG. 4.
Figure 7:
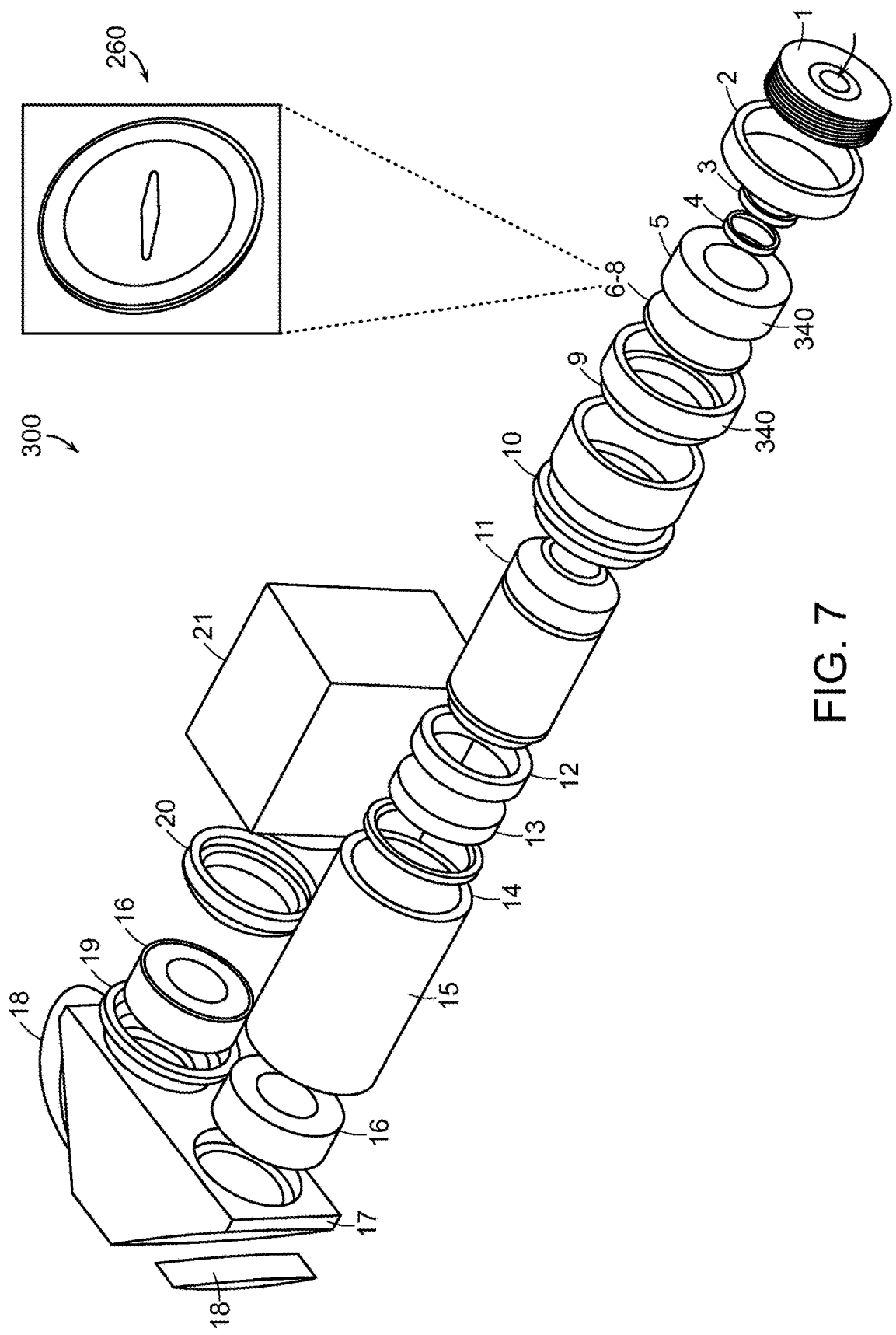
FIG. 7 depicts an exploded view of the module of FIG. 4.

In one illustrative embodiment shown in FIGS. 5-7, a red LED (Thorlabs, LED630E) threaded to a tube mount (Thorlabs, S1LEDM) served as the light source. A glass diffuser positioned between the LED and sample chamber provided uniform illumination across the field of view. The 25 mm diameter of the sample chamber was designed to be compatible with the SM1 lens tube. The sample was magnified and imaged onto a CCD camera (AVT, Prosilica, GC 2450) with a 40× Olympus Plan Achromat objective (infinity corrected, 0.65 NA and 0.6 mm WD) and Ø1" 100 mm tube lens (Thorlab, AC254-100-A). The camera used the standard GigE Vision interface, outputting the data as a gigabit Ethernet signal. To enable live imaging during centrifugation, a fiber-optic rotary joint (PrinceTel, MJX) can be installed at the center of the centrifuge rotor. The camera signal can be converted from twisted-pair Ethernet to a fiber-optic signal by a small media converter inside of the centrifuge, transferred through the rotary joint, then converted back to a standard Ethernet signal by a second media converter connected to the acquisition computer. In one illustrative example, the MiniMc Gigabit products, from IMC Networks, (e.g., part numbers 855-10734 and 855-10735) can serve as the media converters. The images collected from the detector can be recorded.

To measure sample temperature, in one embodiment, a portable wireless thermocouple connector (Omega Engineering, MWTC-D-K-915) may be embedded with a surface adhesive thermocouple (Omega Engineering, SA1XL-K) within the bucket that contains the module. A wireless receiver (e.g., Omega Engineering, WTC-REC1-915) can be used to acquire the temperature from the thermocouple connector to record the temperature in real time.

FIG. 6 depicts shows a perspective view of the module alone, without the centrifuge bucket. As can be seen from FIG. 6, the module has a U-shaped arrangement. The first leg 301 and the second leg 302 of the U-shape need not be the same length. In the embodiment shown in FIG. 6, the first leg 301 is longer than the second leg 302. In the illustrative embodiment of FIG. 6, the light source 22, objective 11 and sample holder 340 are located within the first leg 301, and the detector 21 is located within the second leg 302. However, it should be understood that the optical components and sample holder may be arranged in any order and placed in either leg.

It should be appreciated that, in other embodiments, the light source, objective, sample and detector can be aligned, thus eliminating the need for a turning mirror. For example, in larger centrifuges, such as larger floor models with 1 Liter buckets, the greater bucket depth may fit the light source, objective, sample and detector in a line without needing to bend the optical path.

In yet other embodiments, the optical path may have one or more bends at angles other than right angles, e.g., the optical path may have a 15, 30, 45, 60 or 85 degree bend. Such bends may be accomplished using one or more mirrors.

In some embodiments, the module includes a housing 305 that secures the components of the module and ensures a tight fit within the bucket or other volume within the centrifuge. The housing may include an open slot for a battery (e.g., SparkFun, PRT-00339), and a connected DC-to-DC step up circuit (e.g., SparkFun, PRT-08290) to serve as the power source for the light source, detector, and, in some embodiments, media converter. The housing 305 may be 3D printed, injection molded, die cast, or formed by any other suitable method. In some embodiments, the housing is made of acrylonitrile butadiene styrene (ABS) was.

FIG. 7 depicts an exploded view of one illustrative embodiment of the module 300. A list of parts corresponding to each numerical reference number is listed in Table 2 below. It should be appreciated that this list of parts is only one illustrative embodiment, and that other suitable parts may be interchanged with those on the list.

TABLE 2

Parts List of Module

| Reference No. | Name | Vendor | Part Number | Description |
|---|---|---|---|---|
| 1 | Light source mount | Thorlabs | S1LEDM | SM1-Threaded Mount |
| 2 | Coupler | Thorlabs | SM1T1 | SM1 (1.035"-40) Coupler |
| 3 | Retaining ring for diffuser | Thorlabs | SM05RR | |
| 4 | Light source diffuser | Thorlabs | DG05-220 | Ø½" N-BK7 Ground Glass |
| 5 | Diffuser and first half of sample holder | Thorlabs | SM1A6T | |
| 6 | Support glass - first side of sample chamber assembly | SI Howard Glass Co | D265 | Ø 25 mm, 0.7 mm Thick |
| 7 | Double sided tape holding the two glasses (6, 8) together | Kapton Tape | PPTDE-1 | |
| 8 | Cover glass - second side of sample chamber assembly | Electron Microscopy Sciences | 63782-01 | Gold Seal, #1 19 mm |
| 9 | Second half of sample holder | Thorlabs | SM1L03 | SM1 Lens Tube, 0.3" Thread Depth |
| 10 | Focusing lens tube | Thorlabs | SM1V05 | Focusing Ø1" SM1 Lens Tube |
| 11 | Objective | Edmund Optics | #86-815 | 40× Olympus Plan Achromat Objective, 0.65 NA, 0.6 mm WD |
| 12 | Objective Adapter | Thorlabs | SM1A3 | Objective Adapter with External SM1 Threads and Internal RMS Threads |
| 13 | Achromatic doublet | Thorlabs | AC254-100 | f = 100.0 mm, Ø1" Achromatic Doublet, ARC: 400-700 nm |

TABLE 2-continued

Parts List of Module

| Reference No. | Name | Vendor | Part Number | Description |
|---|---|---|---|---|
| 14 | Tube lens retaining ring | Thorlabs | SM1RR | Tube Lens SM1 Retaining Ring |
| 15 | Objective lens tube | Thorlabs | SM1M20 | Objective SM1 Lens Tube Without External Threads, 2" Long |
| 16 | Adapter | Thorlabs | SM1A6T | Adapter with External SM1 Threads and Internal SM05 Threads, 0.40" Thick Aluminum |
| 17 | Housing for turning mirrors | | | |
| 18 | Turning mirrors | Thorlabs | PFE10-P01 | 1" Silver Elliptical Mirrors, 450 nm-20 μm |
| 19 | Camera locking ring | Thorlabs | SM1NT | Camera SM1 (1.035"-40) Locking Ring, Ø1.25" Outer Diameter |
| 20 | Camera adapter | Thorlabs | SM1A9 | Camera Adapter with External C-Mount Threads and Internal SM1 Threads |
| 21 | Detector | Allied Vision Technologies | Prosilica GC2450 | Sony ICX625 CCD sensor, 2448 × 2050 resolution, 15 fps, 12 bit |
| 22 | Light source | Thorlabs | LED630E | Red LED |

In the illustrative embodiment of FIG. 7, parts 5 and 6 combine to form the sample holder 340, and parts 6-8 combine to form the sample chamber 260. Part 5 can have two functions—it forms part of the sample holder and acts as a diffuser. The sample chamber is held within the sample holder. The turning mirrors 18 are held by a housing 17 that connects the mirrors to the rest of the assembly and holds the mirrors at a proper angle. The housing 17 may also serve to connect the first leg of the U-shape to the second leg.

The detector used in the illustrative embodiment of FIG. 7 is equipped with a 5 Megapixel CCD sensor with a maximum frame rate of 15 fps at full resolution. Depending on the application, alternative cameras with different resolutions and acquisition rates could be used as the detector—for example, the Basler Ace CMOS camera at 15 Megapixels or 2 Megapixel version is under $400 (Edmund Optics, Inc.) The media converter (item 22) that converts the twisted wire Ethernet connection to an optical signal could be omitted if a camera with a 10 GigE optical fiber output is used. Data output using a compact wireless router is an alternative approach, but may result in a slower acquisition rate. Additional customized parts such as the turning mirror housing can be replaced with a Thorlabs compact cage cube system. In some cases, a solid aluminum construction may provide added stability of the imaging path.

In some embodiments, the detector may be a wireless video camera, such as an action camera (e.g. GoPro HERO) or a cell phone. The camera can be wirelessly controlled and can wirelessly stream and/or record at full resolution. Such an arrangement would avoid the need to run cables through the centrifuge. In some cases, such an arrangement would also avoid the need for a media converter.

Figure 8:
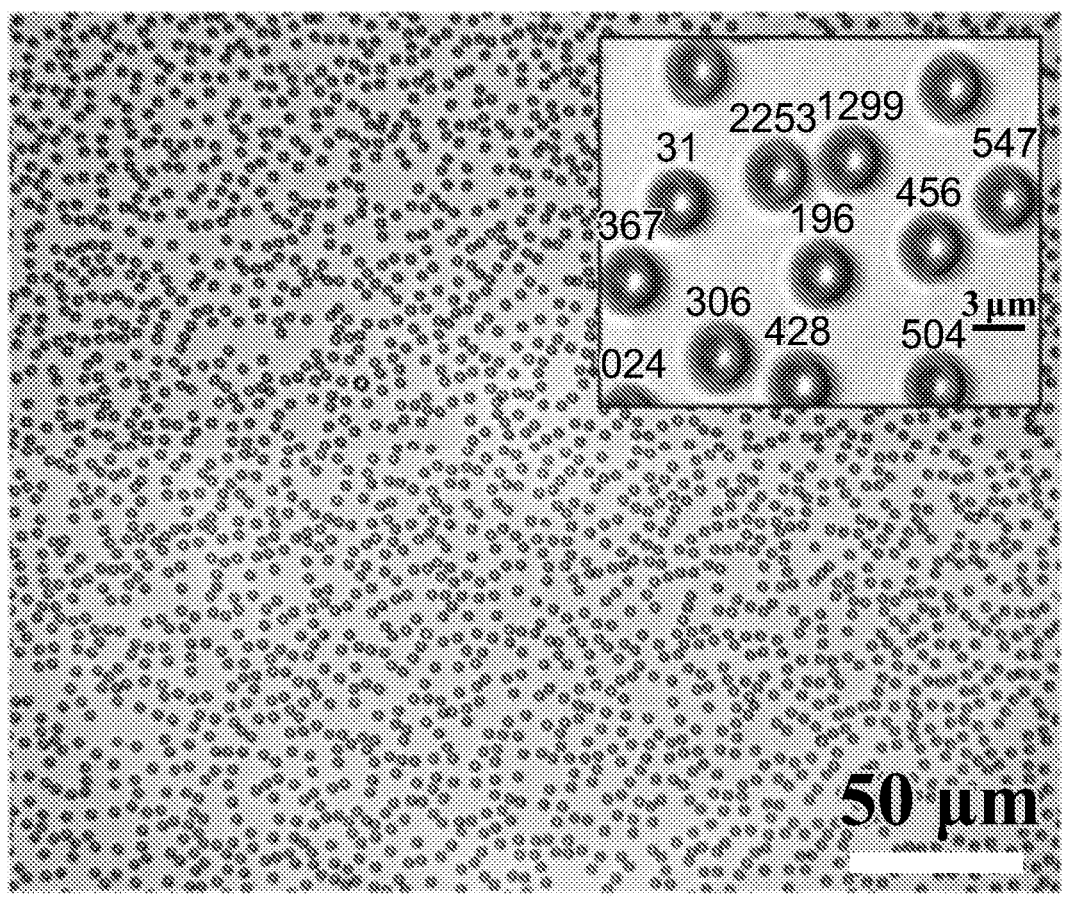
FIG. 8 depicts a typical field of view during a force spectroscopy experiment using the spinning force apparatus.

FIG. 8 depicts a typical field of view during a force spectroscopy experiment using the spinning force apparatus, showing that thousands of surface-tethered beads can be monitored in parallel.

Sample Chamber Construct

In one illustrative embodiment, the sample chamber can be constructed using double-sided Kapton tape sandwiched between a 25 mm diameter support glass and a 19 mm diameter cover glass (Gold Seal, 3346). Two 1 mm diameter ports, which serve as a solution inlet and outlet, are drilled into a 0.7 mm thick support glass (S.I. Howard Glass (D263)). The cover and support glasses can be cleaned by immersing in 100 mL a 1% (v/v) Hellmanex III solution, microwaving for 1 minute, then sonicating for 30 minutes. Subsequently, the slides may be rinsed thoroughly with Millipore water then dried with nitrogen flow. A 1 mm×7 mm rectangular flow channel is cut on the double-sided Kapton tape using a cut plotter (Graphtec). To form tethers with digoxigenin functionalized construct, the cover glass is functionalized with anti-digoxigenin using a modified version of a previously developed protocol[32]. First, the cover glass is coated with a nitrocellulose solution by depositing 2 μL of amyl acetate solution with 0.2% (m/v) dissolved nitrocellulose. The channel is then incubated with phosphate buffered saline (PBS, 137 mM NaCl, 2.7 mM KCl, 10 mM phosphate buffer, pH 7.4) solution containing 100 ug/ml anti-digoxigenin (Roche, 11333089001) for 15 minutes. The channel is then washed and further incubated with a surface passivation solution (10 mg/ml Roche Blocking Reagent in PBS) for 1 hour. After the passivation step, the channel is flushed with experimental buffer then incubated with 5 pM of construct for 15 minutes. At 5 pM construct concentration, the construct may be limited to an average spacing of roughly 2 μm on the surface, which may make formation of double tethers a rare event. After tethering the construct to the surface, the flow channel is washed with 20 uL of the experimental buffer then incubated with 15 mg/ml streptavidin beads (Invitrogen M-270). For each experiment, beads can be washed excessively with the experimental buffer before loading them to the sample chamber. Before loading the sample chamber into the module of the spinning force system, the solution inlet and outlet ports are sealed with vacuum grease. The Tris experimental buffer may consist of 10 mM Tris, 30 mM NaCl at pH 7.5 with or without 10 mM $MgCl_2$.

For the overstretching experiment, the surface tethering was strengthened by replacing digoxigenin-anti-digoxigenin with biotin-streptavidin—in other words, biotin-streptavidin interactions were used to anchor each tether. The nitrocellulose surface was functionalized by incubating it with 1 mg/ml streptavidin in PBS solution that contained 1 mg/ml of Roche Blocking Reagent for 12 hour, followed by incubation with passivation solution (10 mg/ml Roche Blocking Reagent in PBS buffer) for 1 hour. The channel was flushed with PBS and incubated with 5 pM of dual-biotin λ-DNA for 15 minutes before loading in the streptavidin-coated beads. Under such conditions, the density of streptavidin on the surface was sparse enough that only one end of the biotin-labelled λ-DNA bound to the surface, leaving the other biotinylated end free to bind to the streptavidin-coated bead.

Angled Measurement Method

According to one aspect, the inventors have developed a method of measuring nanometer-level extensions of tethers in the spinning force system by projecting tether length changes onto the X-Y plane of the surface to which sample is coupled (e.g. a cover glass or other coverslip), enabling these measurements to be made in a relatively simple and computationally efficient way. The method utilizes the fact that the direction of force application by the centrifuge can be controlled by mechanically constraining the angle of the centrifuge bucket or, in centrifuges without buckets, the holder(s) in the centrifuge that holds sample (e.g. holes into which test tubes or other sample holding containers are inserted). In the method, the direction of centrifugal force and the imaging axis are intentionally misaligned.

The imaging axis is oriented in the direction along the direction in which light from the light source passes through or is otherwise incident to the sample. For example, if the optical components and sample are in a straight line, the imaging axis is defined as the axis along that line. If the optical components and sample are not in a straight line, and devices are used to redirect light, (e.g., mirrors), the imaging axis is oriented along the direction in which light from the light source hits the sample. In the U-shaped configuration of the embodiment of FIGS. 4-6, the imaging axis is the line along which the light source, sample, and objective are aligned.

In some embodiments, a spinning force system is arranged such that the direction of force and the imaging axis are intentionally misaligned in order to track tether extension length by tracking lateral particle motion—i.e., motion of the particle occurring perpendicular to the imaging axis. When the direction of force and the imaging axis are aligned, particles move only in a direction parallel to the imaging axis. In such a situation, change in tether length is difficult to track because all that the detector sees is the tethered particle (e.g., bead) getting larger in size or smaller in size.

When the direction of force and the imaging axis are intentionally misaligned, the detector sees lateral movement of the particle. This information can be used to determine tether extension length.

Figure 9:
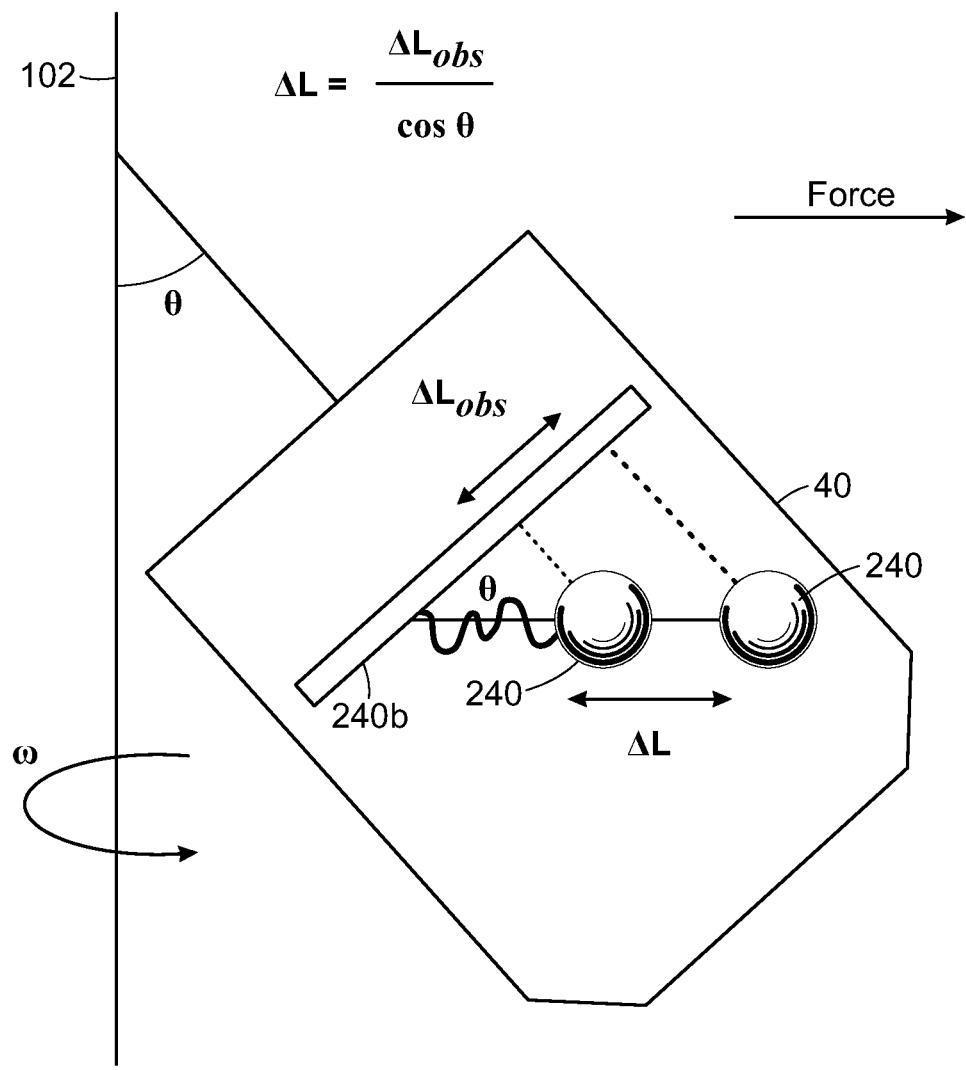
FIG. 9 depicts a schematic of a measurement method according to one embodiment.

Based on the geometry as illustrated in FIG. 9, extension of the molecular tether can be measured by tracking the motion of the tethered particle 240 (e.g., a bead) parallel to the surface to which sample is coupled (e.g. a cover glass or other coverslip). Specifically, changes in tether extension will appear to the detector as a lateral displacement of the bead $\Delta L_{obs}$. The actual changes in tether extension $\Delta L$ in the direction parallel to the force can be calculated based on the angle of the bucket θ relative to the rotation axis 102 as follows:

$$\Delta L = \frac{\Delta L_{obs}}{\cos(\theta)} \quad (3)$$

The minimum tether length that can be measured using this method depends on both the bead size used in the experiment and the angle of the centrifuge bucket relative to the rotation axis. If the tether length is not long enough to allow the bead to be pulled away from the surface 8, the bead may end up making direct contact with the surface 8, which will result in inaccurate measurements. The minimum tether length $L_{min}$ as a function of bead radius $R_{bead}$ and bucket angle θ is given by:

$$L_{min} = R_{bead}\left(\frac{1}{\sin(\theta)} - 1\right) \quad (4)$$

Figure 11:
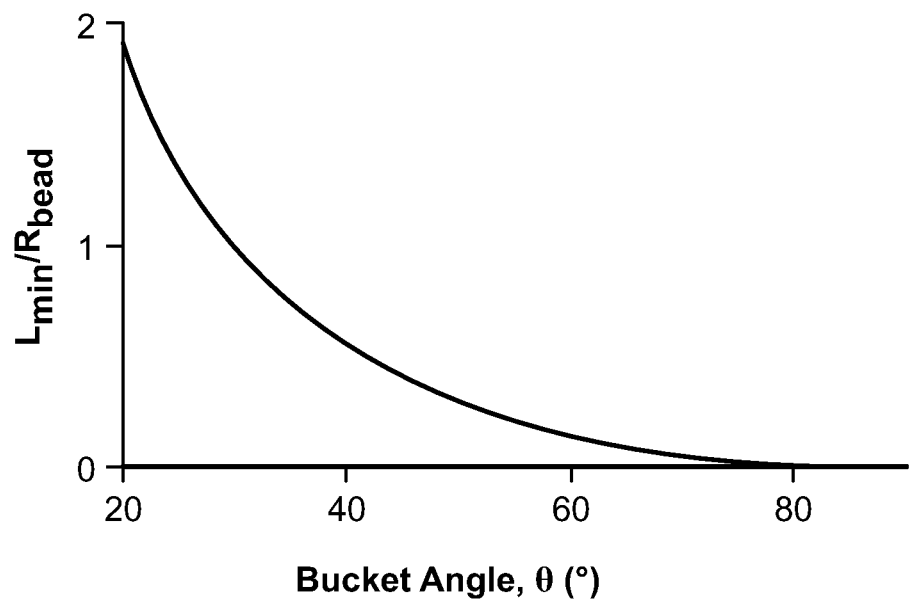
FIG. 11 depicts a graph angle associated with the method depicted in FIG. 9, the graph showing the minimum tether length, scaled by the bead radius, required to measure tether extension from lateral displacement, calculated as a function of the bucket.

FIG. 11 shows the minimum tether length $L_{min}$, scaled by the bead radius, required to measure tether extension from lateral displacement, calculated as a function of the bucket angle θ.

The angle of the bucket θ relative to the rotation axis can be determined in different ways, depending on the type of centrifuge that is used. With centrifuges having a single fixed angle such as a fixed angle rotor centrifuge or a vertical rotor centrifuge, the angle θ is known, as it does not change. With centrifuges that change angle with changing rotation speed, such as a swinging-bucket rotor, measurements may be needed to determine the angle of the bucket θ associated with different angular velocities.

Figure 12:
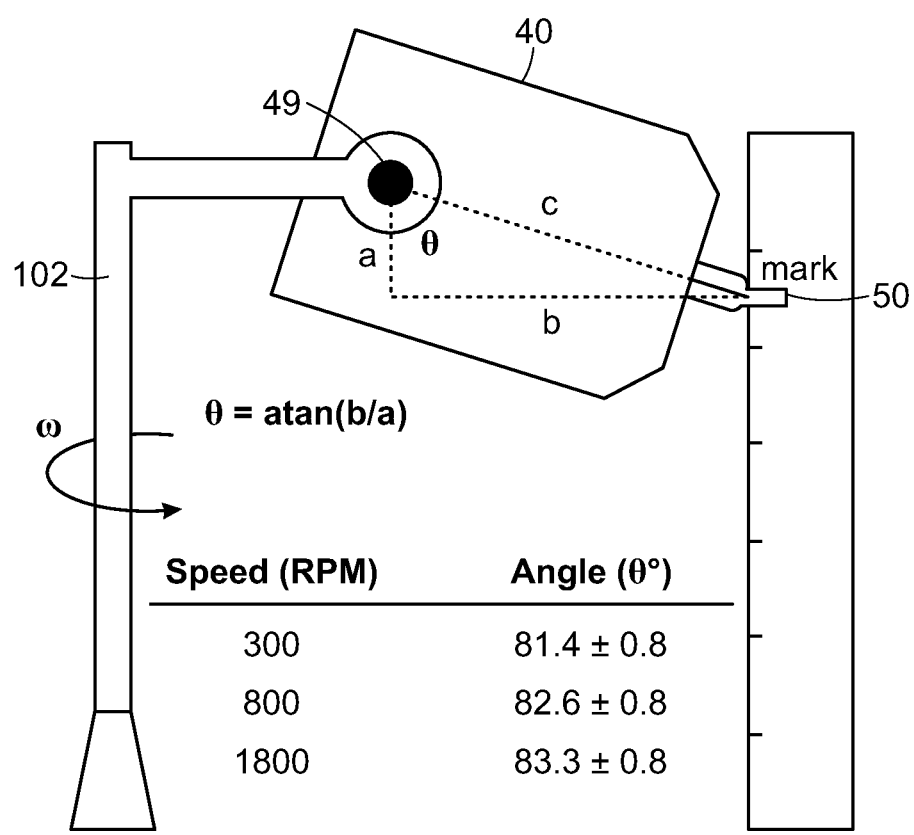
FIG. 12 depicts a schematic of a method of measuring the bucket angle associated with different rotational velocities.

In one exemplary method, illustrated in FIG. 12, a marker or other marking device may be attached to the bottom of a bucket. The marker marks the height of the bucket bottom on the wall as the centrifuge spins. The vertical distance a from the pivot point 49 to the mark 50 and the horizontal distance b from the pivot point 49 to the mark 50 are measured. With these known distances, the angle of the bucket relative to the rotation axis is given by:

$$\theta = a\tan(b/a) \quad (5)$$

In one experiment using the arrangement of FIG. 12, the uncertainty of the angle measurement was based on the distance measurement error estimate of 1 mm. At the angular velocity of 300 RPM, the bucket swung out to an angle of (81.4±0.8)°. At a much higher speed of 1800 RPM the angle increased by 2.3%. Further increase of the angular velocity did not increase the angle beyond the error of the measurement.

Figure 10:
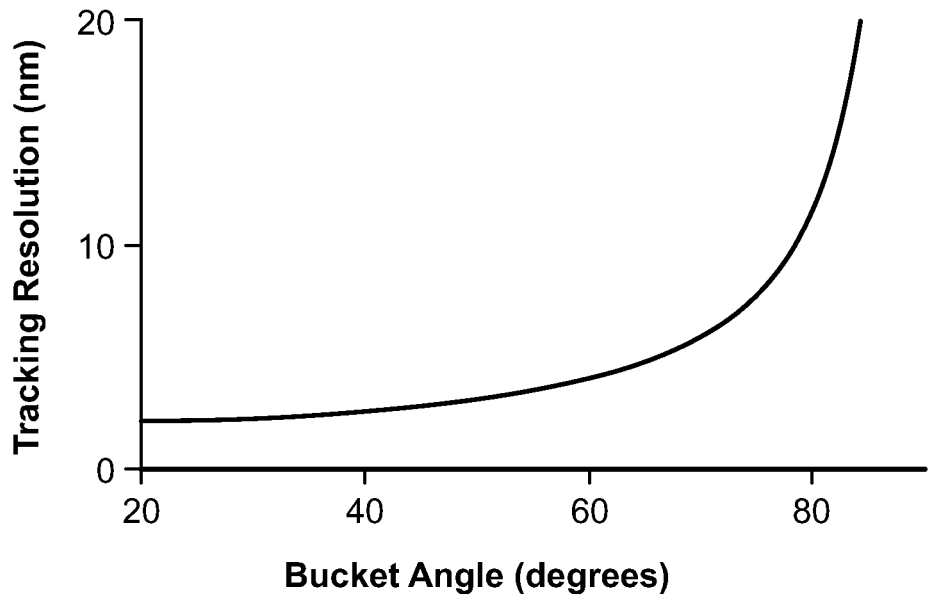
FIG. 10 depicts a graph associated with the method depicted in FIG. 9, the graph showing tracking resolution of tether extension for various bucket angles.
Figure 13:
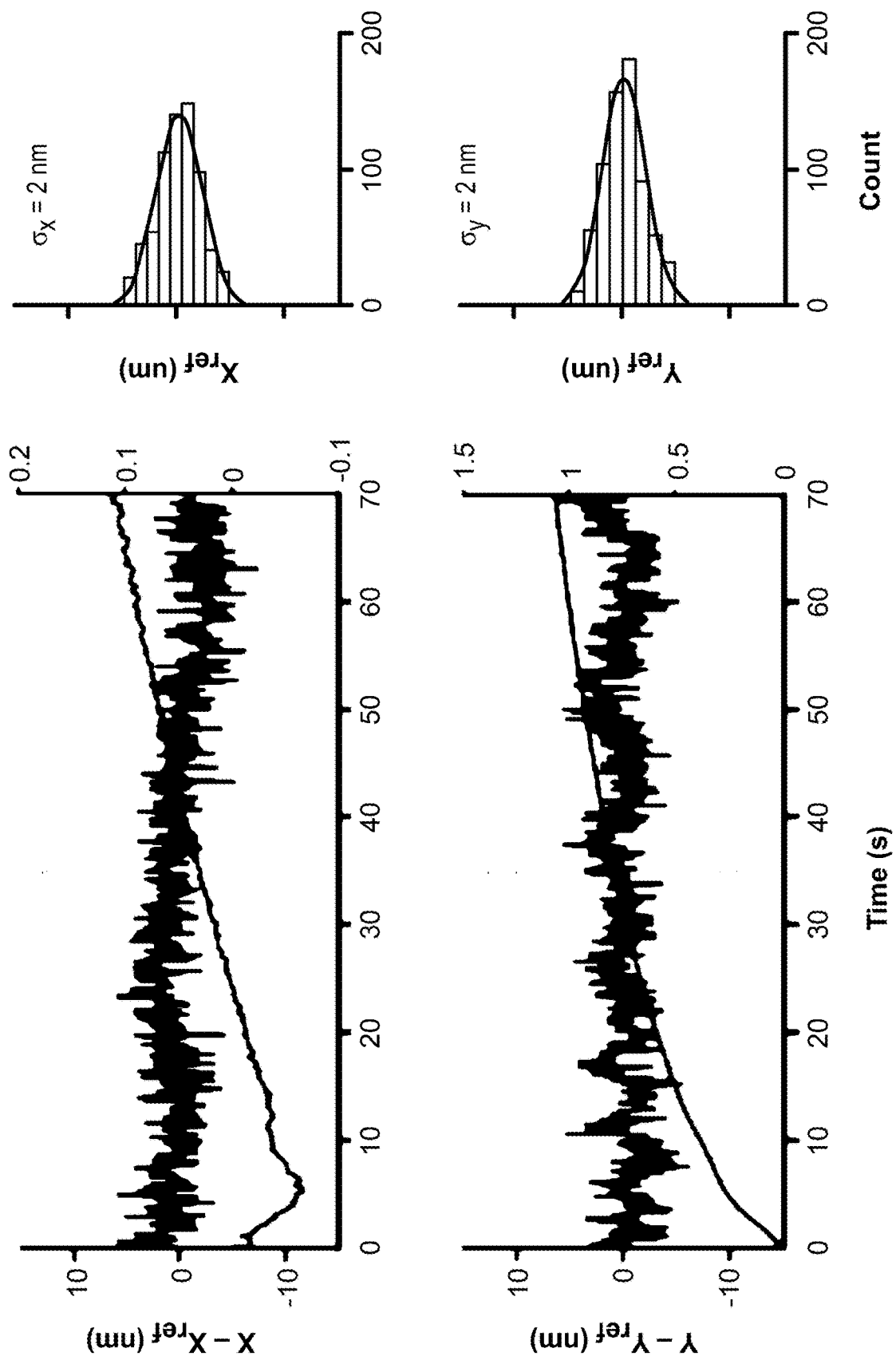
FIG. 13 depicts data from one experiment using the method depicted in FIG. 9.
Figure 14A:
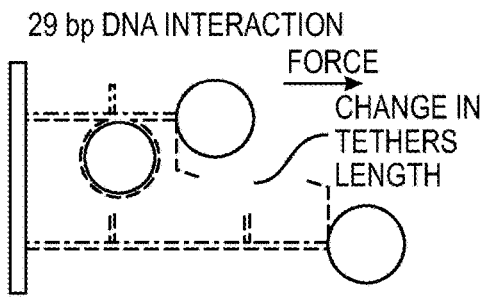
FIG. 14 depicts a schematic of a DNA nanoswitch construct in a looped and an unlooped state, and data associated therewith.
Figure 14B:
Figure 14B:
Figure 14C:
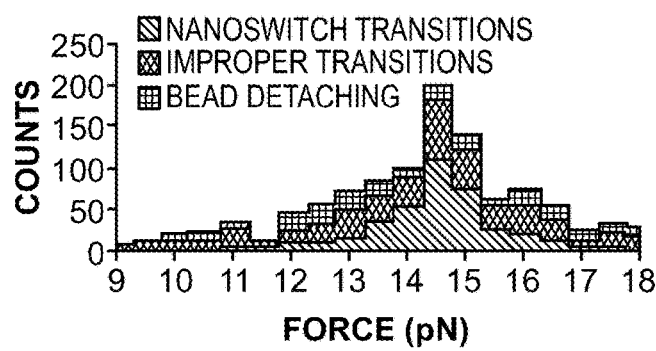
Figure 14D:
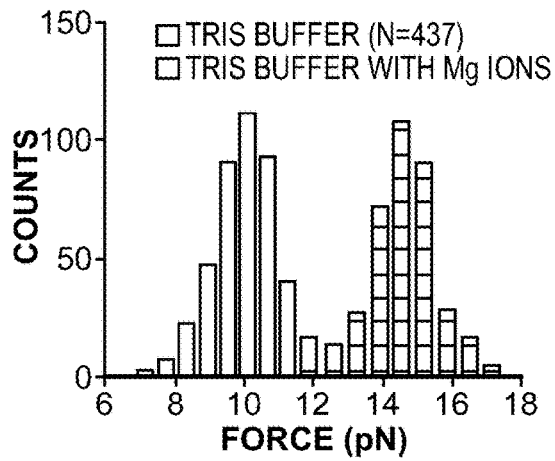
Figure 14E:
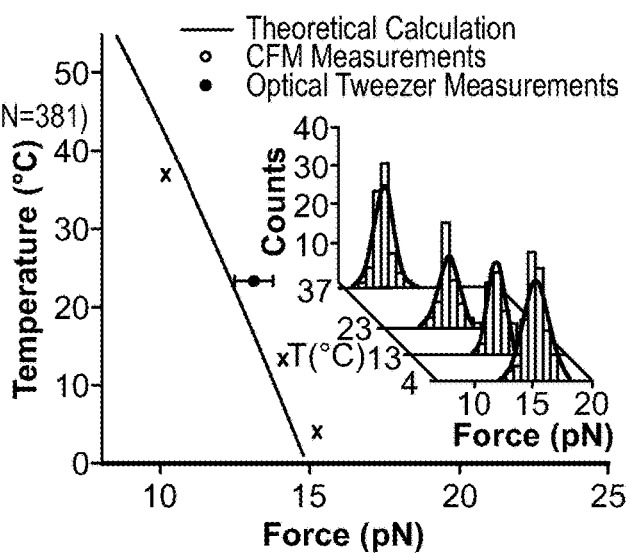
Figure 15A:
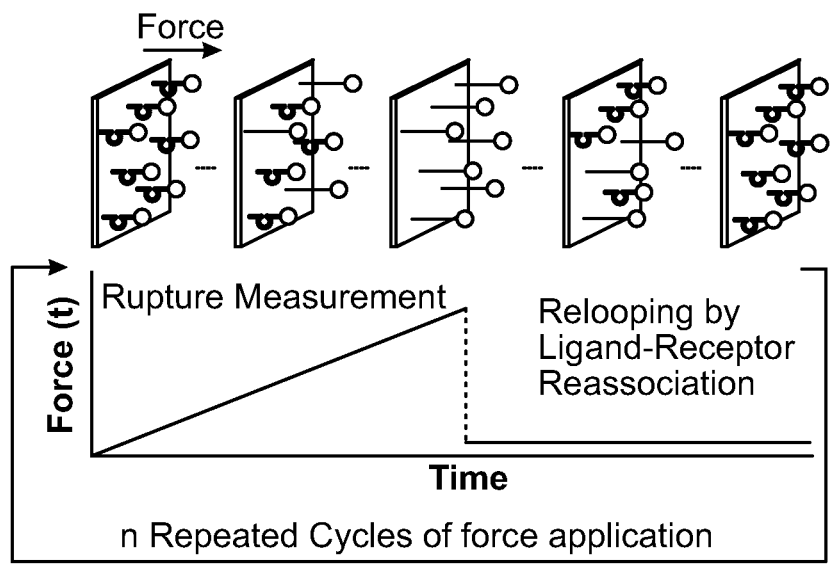
FIG. 15 depicts graphs associated with repeated rupture force measurement of single molecular pairs.
Figure 15B:
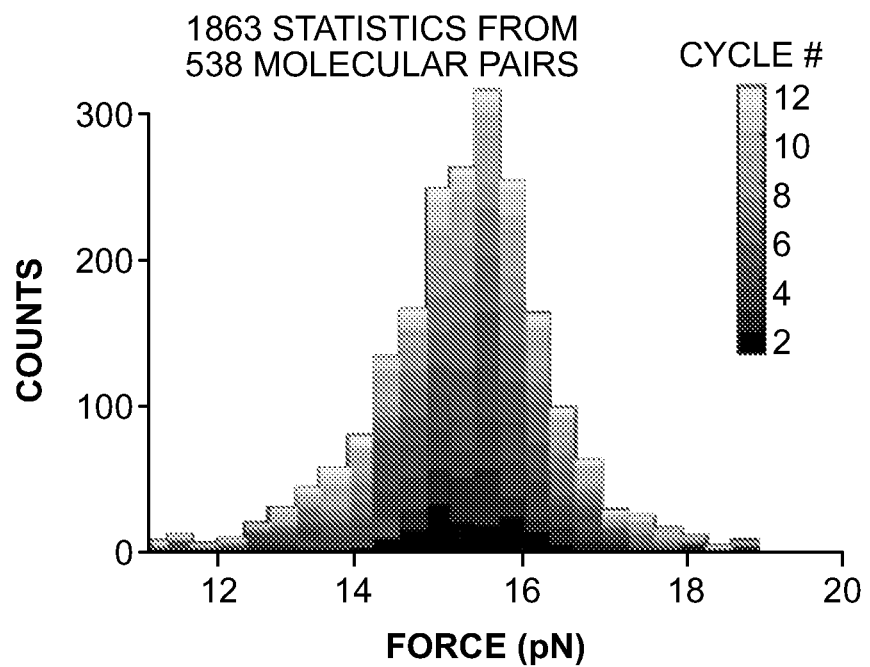
Figure 15C:
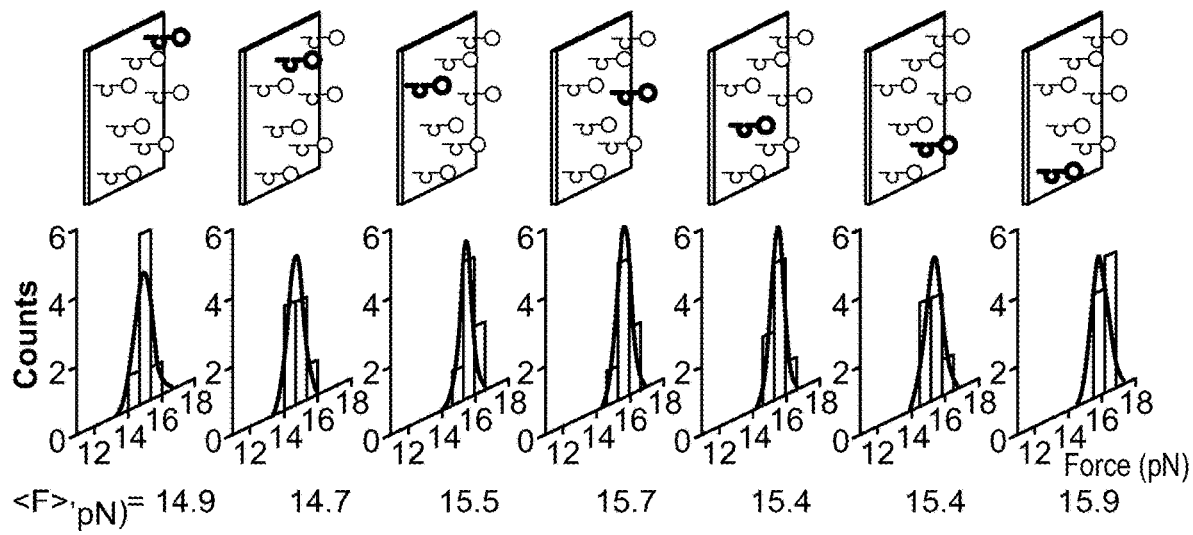
Figure 15D:
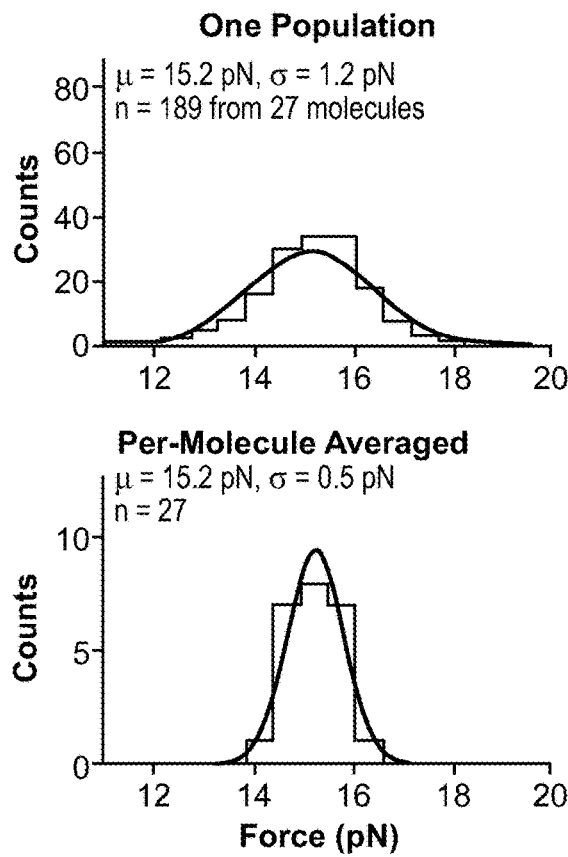
Figure 15E:
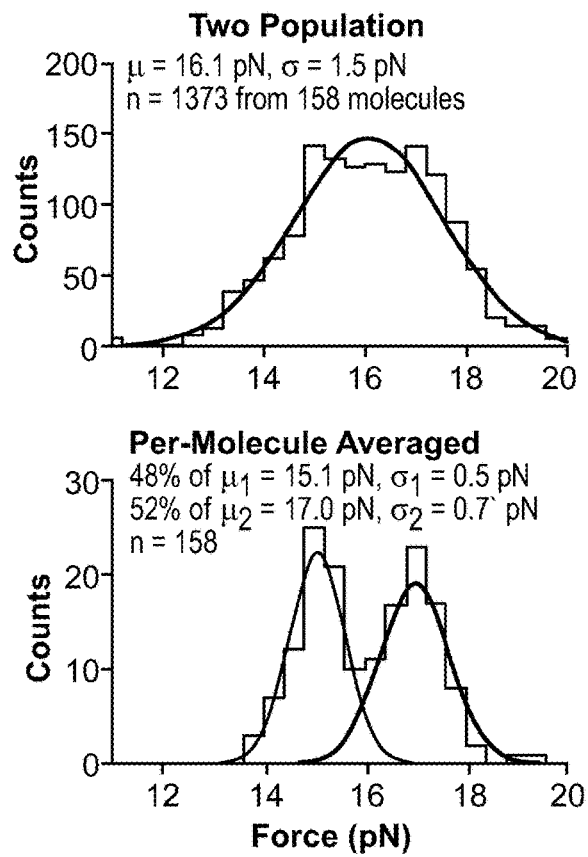

FIG. 10 shows tracking resolution of tether extension for bucket angles between 20° to 85° from one example using this method. Using the angled measurement method, tether length resolution can be "tuned" based on the bucket/sample holder angle with a range of approximately 2.5 nm (at) 20° to 12 nm (at 80°) based on a lateral tracking resolution of ~2 nm. Data from one example using this angled measurement method is shown in FIG. 13. The drift-corrected X and Y position of a 5 um silica bead as a function of time recorded in the centrifuge spinning at 2,000 RPM is shown as the zigzagging line. The drift in X and Y position as a function of time, based on the average position of 12 immobile reference beads, is shown as the smoother trend curve. The panels to the right show histograms of the position with normal distribution fits. Standard deviations of the fits for x and y positions are both ~2 nm. While the standard deviation listed here represents the particle-tracking resolution, the overall accuracy with which tether lengths can be measured also depends on the intrinsic thermal fluctuations of these beads.

To validate and demonstrate this angled measurement method, DNA force-extension for over 100 molecules were measured simultaneously over a span of less than 1 minute, and each were fit with the standard worm-like chain model. The most likely contour length and persistence length was 8.2±0.2 μm and 46±1 nm, respectively, in agreement with expected values[24]. Additionally, multiplexed overstretching measurements of lambda DNA were performed, yielding an overstretching force of 63.5±1.7 pN (mean±SD), consistent with previous measurements at these conditions[24].

FIG. 16 shows parallel DNA force-extension and overstretching measurements made with a spinning force system. Panel A of FIG. 16 depicts force-extension data of half lambda DNA (24 kbp) obtained from a single sample with 113 DNA tethers using a centrifuge bucket constrained to a 20° angle. The top panel shows a scatter plot of the persistence length and contour length obtained from fits to the worm-like chain model performed for each tether (n=113). Histograms projecting the persistence length and contour length of the model onto the x- and y-axis, respectively, are shown as straight lines indicating expected values. The bottom panel shows the force-extension curves of single-tethered DNA data filtered by persistence length and contour length (n=30). Ranges were selected from the peaks of the histograms (one bin-width on either side), yielding filtering ranges of 43-48 nm and 7.8-8.6 µm for the persistence length and contour length, respectively. The overlaid curve represents the expected force-extension curve.

Panel B of FIG. 16 depicts multiplexed DNA overstretching measured with the spinning force system. The top panel shows a representative force-extension curve near the overstretching transition. The overstretching force was extracted as the half-way-point of the two overstretching transition forces and is shown as a vertical line between the dashed vertical lines. The bottom panel shows a histogram of the overstretching force measured from a single sample (n=29) with an average and standard deviation of 63.5±1.7 pN.

Nanoswitches for Authenticating Single-Molecule Data

Figure 17A:
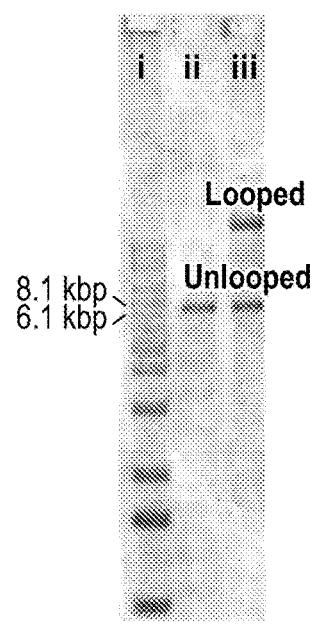
FIG. 17 depicts images associated with verification of the DNA unzipping nanoswitch construct.
Figure 17B:
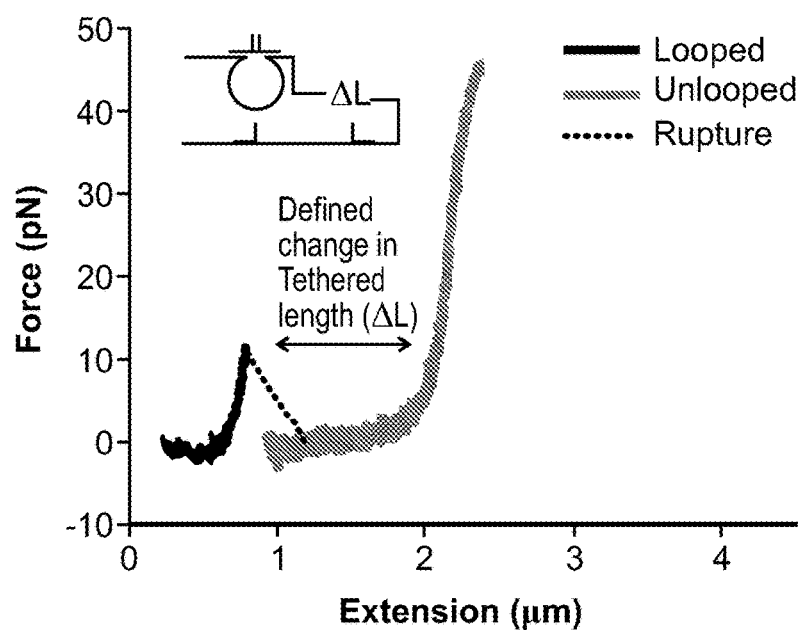
Figure 17C:
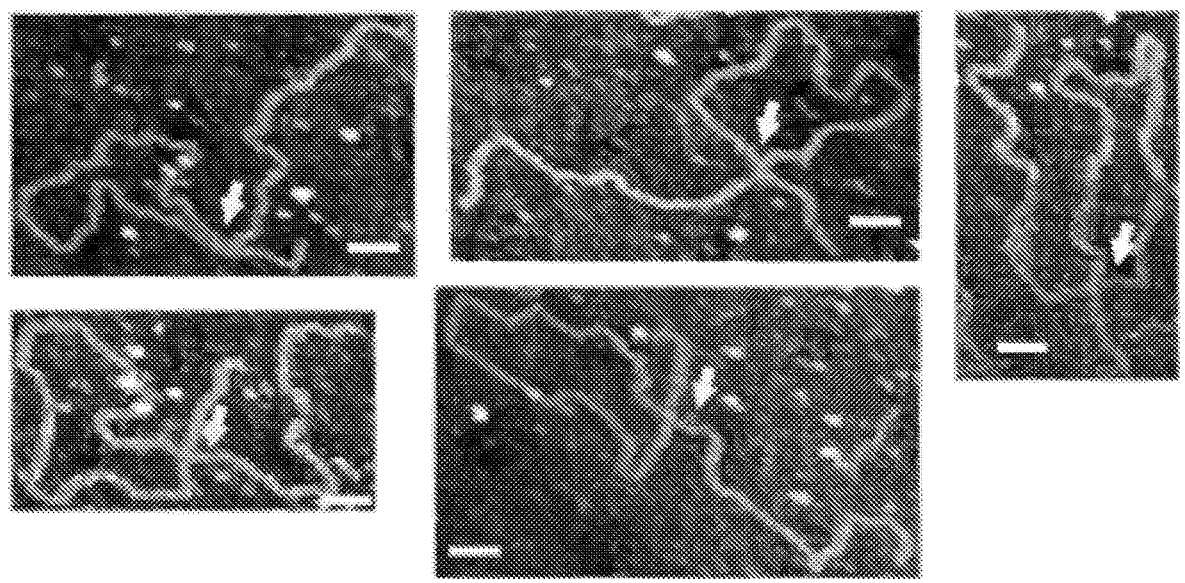
Figure 18B:
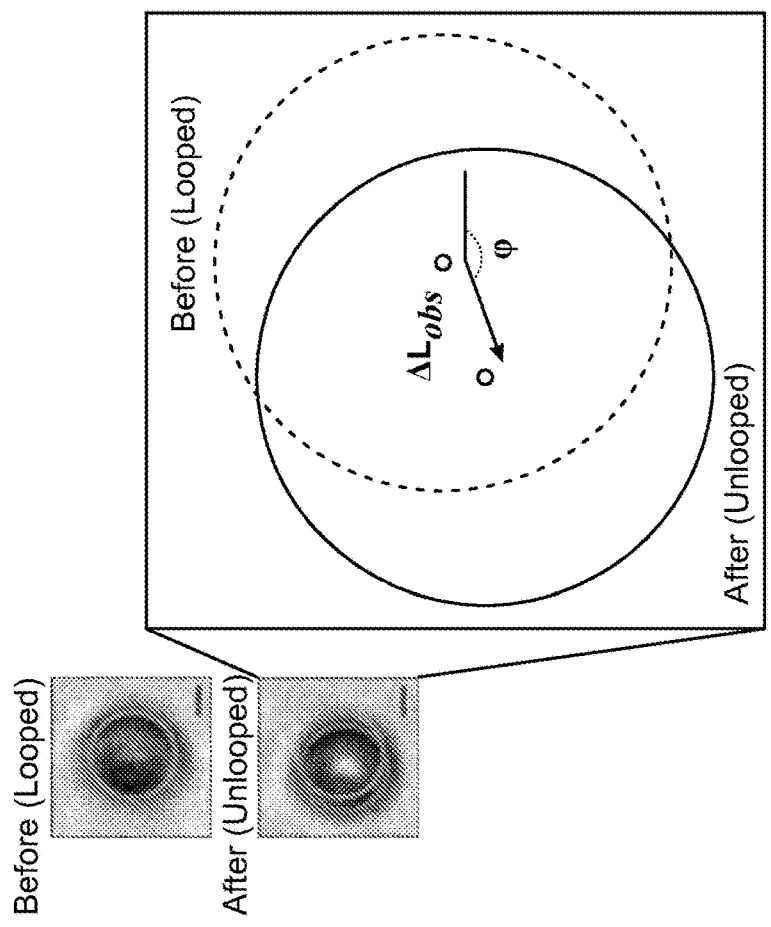
FIG. 18 depicts a schematic of a DNA nanoswitch construct being subjected to the method shown in FIG. 9 and associated data graphs.
Figure 18A:
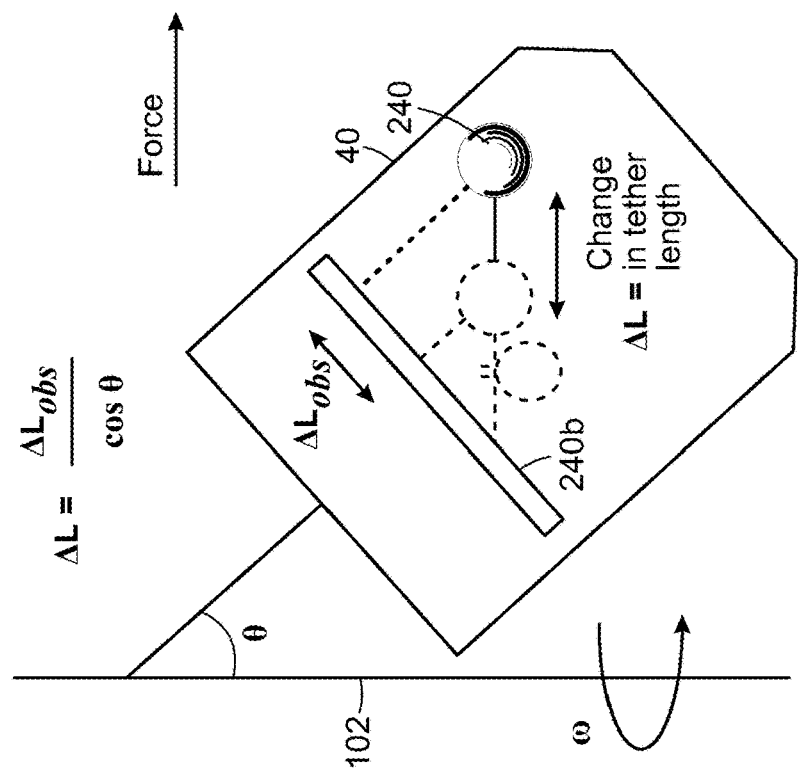
Figure 18C:
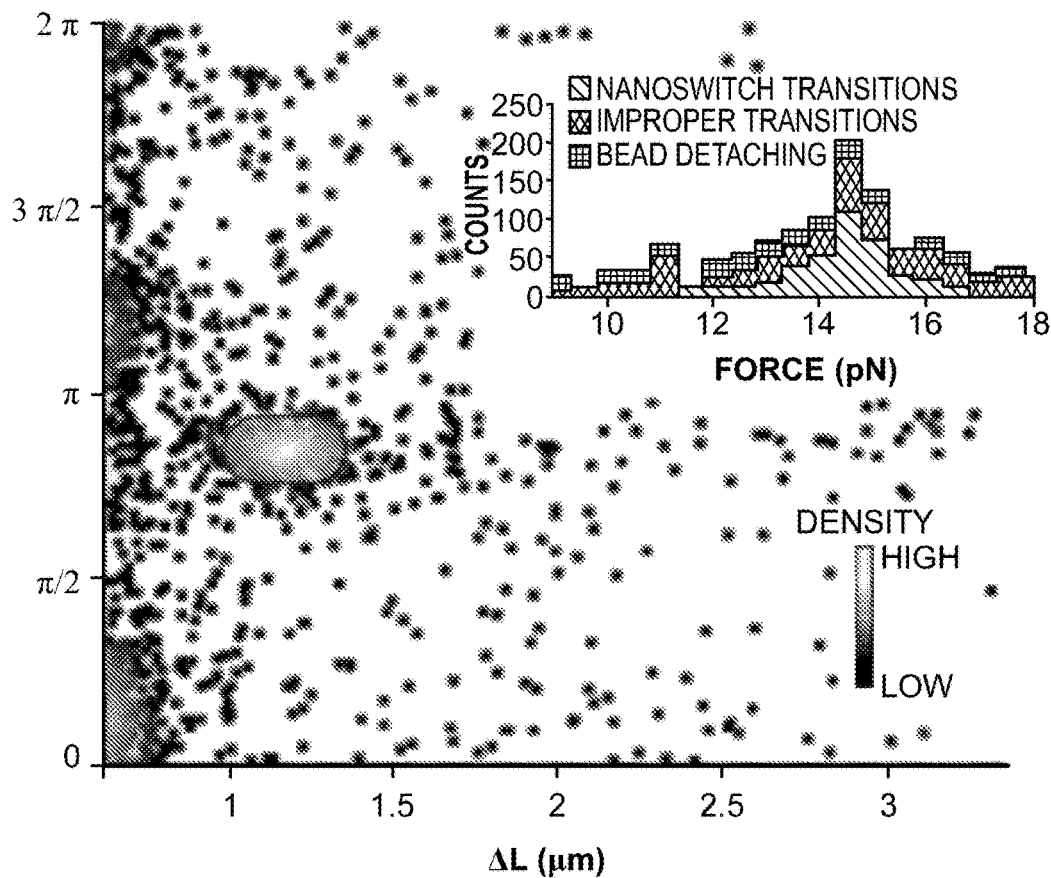
Figure 18D:
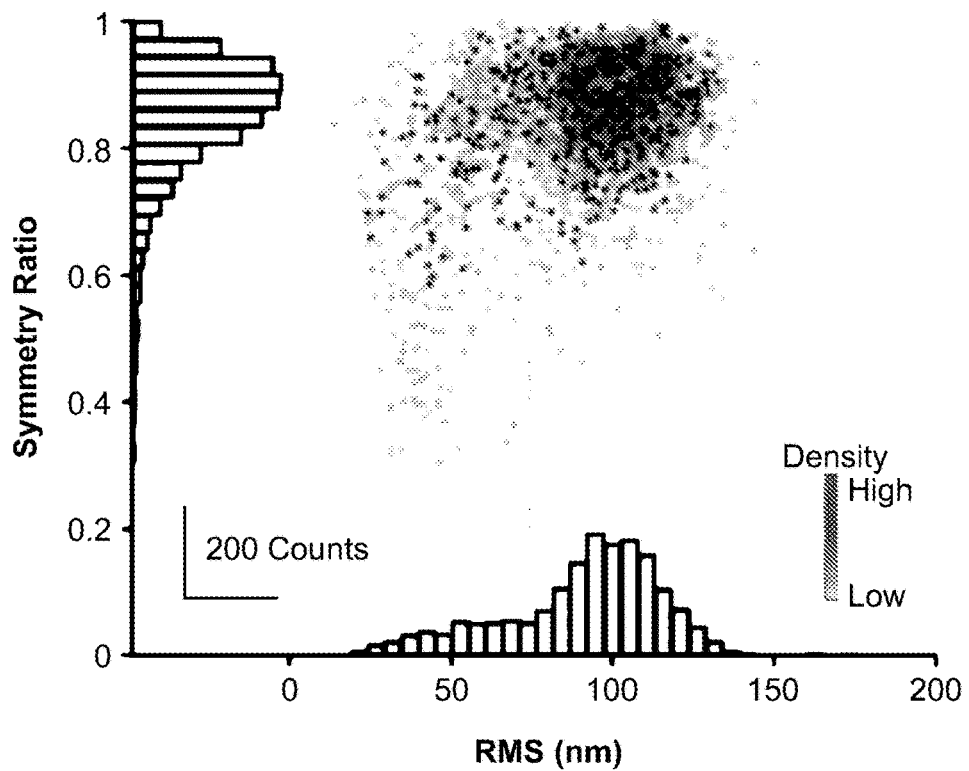

According to one aspect, nanoswitches such as nucleic acid nanoswitches are used with the spinning force system. The inventors have recognized that the use of nucleic acid nanoswitches, such as DNA nanoswitches, with the spinning force system can help to enable robust and repeatable rupture experiments. In some embodiments, these molecular switches are designed to adopt a looped structure when the molecules of interest are interacting and a linear structure when they are not, as seen in FIG. 14, panel A. As a result, nanoswitches provide a distinct "signature" (i.e. increase in tether length) for rupture events, as seen in FIG. 17, panel B.

In one example, DNA unzipping experiments were performed on a 29 bp DNA interaction, and the "signature" unlooping of the nanoswitches was used to positively identify and discriminate valid single-molecule data from multiple tethers and non-specific interactions.

Panels A of FIG. 14 depicts a schematic of a nanoswitch in a looped and an unlooped state. Two complementary oligos hybridize to form a looped nanoswitch. Force can unzip the two complementary strands, resulting in a measurable increase in tether length, providing a signature of DNA unzipping.

Panel B of FIG. 14 depicts images of a bead tethered to the surface via a nanoswitch showing the looped and unlooped states. The scale bar is 1 µm long.

Panel C of FIG. 14 depicts one example of rupture force measurement. 381 tethers were identified with the nanoswitch transitions signature to collect rupture forces while the remaining 673 transitions that corresponded to bead detachment and improper transitions were omitted.

Panel D of FIG. 14 depicts unzipping force histograms of 29 bp dsDNA measured with the nanoswitch under two different buffer conditions. Unzipping force measurements were carried out in the presence and absence of magnesium ions, with hundreds of rupture statistics for each condition collected in under 30 seconds of centrifuge run time. Magnesium was found to stabilize the duplex, with the average unzipping force (±the standard deviation) increasing from 10.1±0.9 pN to 14.6±1.1 pN with the addition of magnesium.

Controllable Temperature Conditions

The inventors have recognized that it can be desirable to conduct experiments in different controlled temperatures. The inventors have also recognized that many standard centrifuges have built-in temperature control and/or portability to move into cold (e.g., 4° C.) or warm (e.g., 37° C.) rooms. The inventors have appreciated that using these kinds of centrifuges in the spinning force system permits experiments with temperature control.

As an example, DNA unzipping experiments were performed using a spinning force system having a centrifuge with built-in temperature control at four temperatures, 4, 13, 23, and 37° C. Panel E of FIG. 14 depicts the average unzipping force of 29 bp dsDNA under different temperatures with PBS buffer (Total n=306), with histograms of rupture forces shown as an inset. The theoretical line is calculated using a previously described thermodynamic model[29].

Real-time measurements of the sample temperature during experiments were made with a wireless thermocouple embedded within the centrifuge bucket. An increase in the unzipping force with decreasing temperature was observed.

Repeated Interrogation and Super-Resolved Force Spectroscopy

The spinning force system and nanoswitches can be used to repeatedly interrogate a population of molecules (or interactions) at the single-molecule (or single interaction) level. In one example, FIG. 15 depicts graphs associated with repeated rupture force measurement of single molecular pairs.

Panel A of FIG. 15 depicts a protocol for repeated cycles of force application, with each cycle consisting of a linear force ramp to induce rupture and nanoswitch unlooping, followed by a low force reassociation period allowing the molecular pairs to rebind.

Panel B of FIG. 15 depicts a DNA unzipping force histogram of 1863 rupture events collected from a total of 538 molecular pairs with 12 cycles of force application. The gradient from darkest to lightest corresponds to statistics collected from each cycle. This data demonstrates the large amounts of single-molecule force data that can be accumulated with this approach.

The nanoswitches enable the unique properties of each molecule in a sample to be characterized from repeated measurements, as demonstrated by determining a rupture-force histogram for each molecule in a sample, illuminating population heterogeneity at the single-molecule level. Panel C of FIG. 15 depicts exemplary rupture force histograms generated for individual molecular pairs. The calculated average rupture force is shown below the graphs.

Furthermore, by averaging data from multiple pulls of the same molecular pair, the spread in force is reduced without losing the unique characteristics of each molecule. When applied to data from a single population, this per-molecule (or per interaction) force averaging generates a super-resolved histogram with the expected narrowing when compared to the raw histogram of all the data. Panel D of FIG. 15 depicts a combined histogram of rupture forces from 27 molecules with 7 cycles of force rupture each (top), and histogram of the per-molecule averaged rupture force (bottom), showing a reduced width.

When applied to combined statistics from two populations of DNA zippers (introducing another G-C rich zipper with a higher unzipping force[30]), the super-resolved histogram generated from per-molecule averaging can separate out two populations that are unresolveable from the raw histograms due to the intrinsic broadening of force that results from thermal noise and instrumental noise. Panel E of FIG. 15 depicts a combined histogram for two populations of DNA unzipping experiments (top), and the per-molecule averaged super-resolved histogram (bottom) that recovers the two separate populations from the mixed data.

Multiple rupture events can be collected for each molecule in a set by repeatedly spinning the same sample multiple times. For the data presented in FIG. 15, panel B, the sample was spun up with an effective force loading rate of 1 pN/s to a maximum force of 22 pN. The speed was then ramped down to zero rpm for approximately 1 hour to allow rebinding between each pair of molecules. Beads were identified from cycle to cycle by their positions relative to a set of fiducial beads which were common to each cycle. For the measurement of the two populations of molecules, two different DNA nanoswitch unzipping constructs were made, one with 48% GC content (CACGAATTCTCTGCCTCCCTTTTAACCCTAG, SEQ ID NO: 1) and one with 31% GC content (CTCAAATATCAAACCCTCAATCAATATCT, SEQ ID NO: 2).

Example of a Nanoswitch Construct Method

In some embodiments, looped nanoswitches, such as DNA nanoswitches, can be made according to the following exemplary process. Circular M13mp18 singlestranded DNA (ssDNA) (New England Biolabs, N4040S) was linearized by hybridizing a 40 bp oligo that created a double-stranded restriction site for the BtsCI enzyme (New England Biolab, R0647S). Subsequently, a set of complementary oligos (Integrated DNA Technologies) was hybridized onto the linear ssDNA. Functionalized oligos (biotinylated and digoxigenin-modified) were hybridized onto the 3' and 5' ends of the ssDNA respectively. The hybridization was carried out with 15 nM of linearized ssDNA and 10 molar excess of the complementary oligos in 1× NEbuffer 2 with a temperature ramp from 90 to 20° C. (−1° C./minute) in a thermocycler. After this initial hybridization two specific single-stranded regions remained, which were bridged by two partially-complimentary oligos to form the final looped construct. The sequence of the complimentary bridge oligo that formed the loop was: CTCAAATATCAAACCCTCAATCAATATCT, SEQ ID NO: 2. This secondary hybridization step was carried out at a final construct concentration of 250 pM with a 1.25 molar excess of the bridge oligos in 1× NEbuffer 2 at room temperature for 1 hour.

Looping of the construct was verified using gel-shift assays, single-molecule optical trap measurements, and AFM imaging, as seen in FIG. 17. FIG. 17 depicts images associated with verification of the DNA unzipping nanoswitch construct. Panel A of FIG. 17 depicts gel electrophoresis of the DNA nanoswitch showing loop formation. Lane i is the 1 kbp extension ladder (Invitrogen, 10511-012), lane ii is a linear construct without the two complementary oligos that close the loop, and lane iii is the nanoswitch construct with the two complementary oligos that can form the looped nanoswitch. The looped DNA migrates more slowly in the gel than the linear construct, resulting in a discrete band with a higher apparent molecular weight as previously observed[36,37].

Panel B of FIG. 17 depicts a force-extension curve of the DNA unzipping nanoswitch construct measured using optical tweezers. The line to the left corresponds to the looped construct, and the line to the right corresponds to the unlooped construct. When forces above ~12 pN were applied, the 29 bp dsDNA that formed the loop unzipped, causing the tether length to increase to the full length of the M13 dsDNA tether.

Panel C of FIG. 17 depicts AFM images of a DNA unzipping nanoswitch construct. The arrow indicates the putative location of the hybridized DNA zipper. The length of the scale bar is 100 nm.

In the optical trap measurement, force was applied on the looped DNA construct via tethering between laser-trapped streptavidin and anti-digoxigenin functionalized silica beads.

For the DNA overstretching measurements in the spinning force system, both ends of lambda DNA was functionalized with biotin to provide strong anchorage to the streptavidin functionalized cover glass and bead surfaces. First, 20 µL of lambda DNA (0.28 ug/ml, Roche, 10745782001) was incubated for 20 minutes at 65° C. to remove the hybridized overhangs. Subsequently, a nucleotide mixture that consists of Biotin-14-dATP, Biotin-14-dCTP, dTTP and dGTP, each at 100 µM final concentration, was added to the lambda DNA solution with 0.25 U/ml Klenow Fragment (New England Biolabs, M0212S). This mixture was incubated for 1 hour at 37° C. The dual-end biotin lambda DNA was purified from the excess nucleotides and enzyme using the Qiagen PCR Purification Kit.

For the parallel force-extension measurements, the half-length lambda DNA was made functionalized with digoxigenin and biotin. First, the biotin-labeled full-lambda DNA construct was cut near the middle using the XbaI restriction enzyme (New England Biolab, R0145S). The resulting overhangs were functionalized with digoxigenin to produce a heterobifunctional 24 kbp construct labeled with digoxigenin on one side and biotin on the other.

Angled Measurement Method with Nucleic Acid Nanoswitch Constructs

When a nucleic acid nanoswitch construct, such as a DNA nanoswitch, is used with the angled measurement method discussed above, the loop opening signature can be identified by tracking the beads' X and Y positions. With the imaging axis and the direction of centrifuge force being at an angle, a component of the centrifugal force is directed in the X-Y plane, as seen in FIG. 18, panel A. As the rotational speed of the centrifuge increases, the looped DNA tethers continuously extend. The opening of the loop can be identified as a discontinuous change in extension. Panel A of FIG. 18 depicts images of a bead before (above), and after (below) a loop opening transition. A bead which is tethered to the surface with a single DNA nanoswitch will undergo a discontinuous change in position with a well-defined length $\Delta L_{obs}$, and direction φ.

In one exemplary experiment, each movie taken contained approximately 1000 beads. To track these beads, they were first identified using the Matlab function imfindcircles. A template image for each bead was stored. To identify the bead in the subsequent frame, the template image was scanned in the X-Y plane to find the position of maximum correlation. First, the image was scanned in the X direction over a 25 pixel search region centered on the bead position from the previous frame. A $2^{nd}$ order parabola was then fit to the correlation coefficient as a function of position. The position of maximum correlation was identified as the new bead position. The template image was than centered on the new X position, and the same procedure was done in the Y direction. During the course of each experiment, there was some drift in the X-Y plane. This was corrected for by taking the median change in X and Y for all beads being tracked from frame to frame. This drift correction can be sufficient for identifying the looped to un-looped transition.

Panel B of FIG. 18 depicts a scatter plot of all contour length changes detected for all directions. The gradient represents data density. Only transitions within the boxed region are accepted as nanoswitch transitions. Inset, a histogram of transition forces for three different types of transitions: beads which leave the surface ("beads detaching"), beads which display discontinuous transition with ("nanoswitch transitions") and without ("improper transitions") correct direction and magnitude. Panel C of FIG. 18 depicts a scatter plot of the symmetry ratio and root mean square displacement based on the lateral fluctuations of all tracked beads, with the gradient representing data density. The overlaid black data points are for tethered beads that undergo validated nanoswitch transitions.

As shown in FIG. 18, panels B and C, transitions were identified by filtering out all bead trajectories except those that contained a discontinuous change in extension of both the correct magnitude and direction. This removed false transitions that may have resulted from non-specific interactions or the formation of multiple bonds between the bead and the surface. Following this automated filtering procedure, the transition events were visually inspected, in random order, to reject any remaining erroneous transitions, which may have occurred due to particle tracking artifacts that manifest as discontinuous changes in position (e.g., particle mislabeling, overlapping beads, etc.).

For DNA unzipping experiments, the number of transitions as a function of time was converted to the number of transitions as a function of force as follows: the rotational speed of the centrifuge was recorded during each movie using WinMess software (provided by Thermo Fisher Scientific, R&D) which enables communication and control with the computer. The rotational speed was then converted to force (F) as a function of time using the following equation:

$$F = m_{bead} R \omega^2 \qquad (6)$$

where R and ω are the rotational radius and rotational velocity, respectively. To determine the effective mass of the beads ($m_{bead}$) in solution, the Invitrogen M-270 bead density was measured through sink-float analysis using aqueous sodium polytungstate solution (Sigma-Aldrich, 71913). A density of $1.61 \pm 0.02$ g/cm$^3$ was obtained, which that confirmed the manufacturer's (Life Technologies) reported value of 1.6 g/cm$^3$. The manufacturer also provided the bead diameter of our specific lot giving a mean of 2.80 um with <1.6% CV (lot #144315600). The density of the silica beads used in the DNA force extension and overstretching experiment was measured similarly using the sodium polytungstate solution, yielding a density of $1.50 \pm 0.03$ g/cm$^3$. The diameter of the silica beads was measured using transmission electron microscopy (TEM), yielding an average and standard deviation of $4.27 \pm 0.16$ um.

FIG. 18 depicts a schematic of a nucleic acid nanoswitch construct, such as a DNA nanoswitch, being subjected to the angled measurement method described above, in which the direction of force and the imaging axis are intentionally misaligned, e.g. the centrifuge bucket is at an oblique angle to the rotation axis and the surface to which the sample is coupled is at an oblique angle to the rotation axis, the detector sees lateral movement of the particle. The centrifuge bucket is at an angle θ relative to the rotation axis, and thus the centrifugal force has components both perpendicular and parallel to the sample surface 240b, which defines the X-Y plane. When the bond is ruptured, the nanoswitch goes from looped (left) to unlooped (right) experiencing a change in length ΔL. This is identified by measuring the projected change in length in the X-Y plane $\Delta L_{obs} = \Delta L \cos \theta$.

Figure 19B:
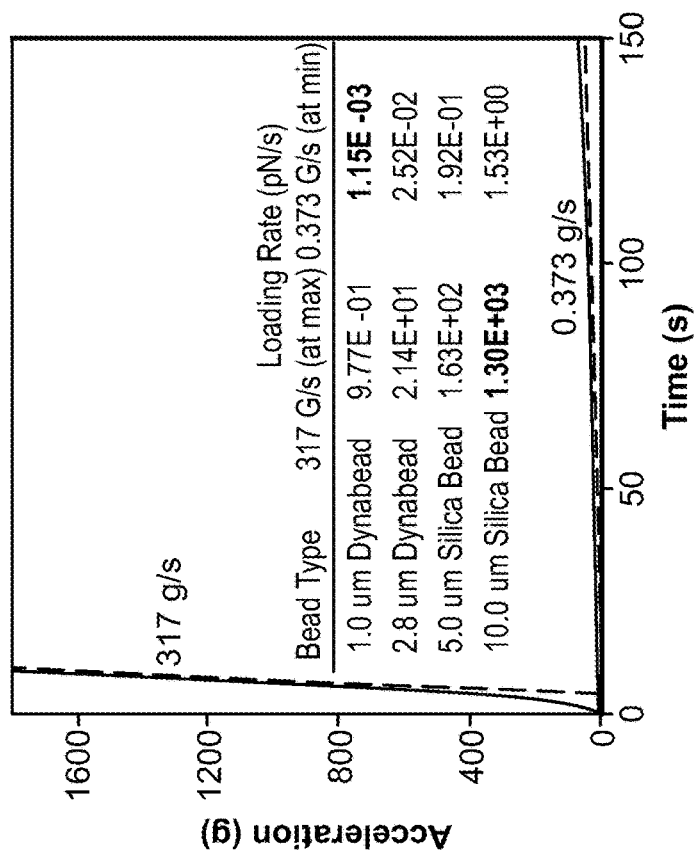
FIG. 19 details the force and loading rate of a spinning force system.
Figure 19A:
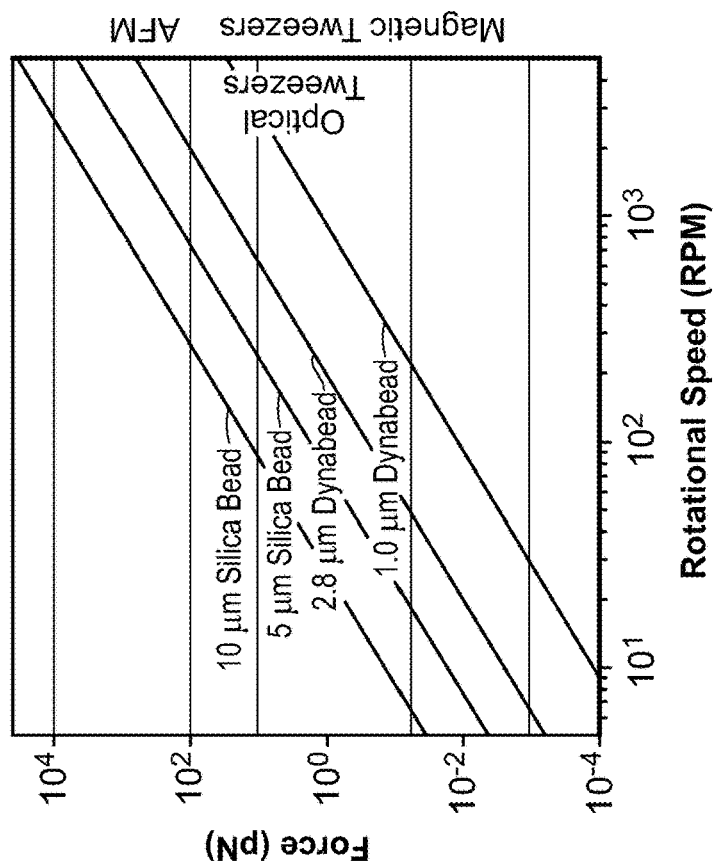

The graphs of FIG. 19 depict the force and loading rate range of a spinning force system, showing that the system has a biologically-relevant dynamic force range. Panel A of FIG. 19 depicts a graph of force as a function of rotational speed calculated using four different types of beads (1 and 2.8 um Dynabeads, and 5 and 10 um silica beads) for a spinning force system using a benchtop centrifuge. Using this set of beads, the spinning force system is capable of applying a force range that spans eight orders of magnitude ($10^{-4}$ to $10^4$ pN).

Panel B of FIG. 19 depicts the fastest and slowest force-loading rates of the spinning force system measured using the Thermo Scientific Heraeus X1R Centrifuge. The fastest ramping rate of 317 g/s, shown in the line to the left, can correspond to a 1,300 pN/s loading rate using a large 10 um silica bead. The slowest ramping rate of 0.373 g/s, shown in the line to the right, can correspond to a 1.15 fN/s loading rate using a small 1.0 um Dynabead (Invitrogen).

Nanoswitches Generally

The nanoswitches of this disclosure minimally comprise a scaffold or backbone nucleic acid comprising one or more, and typically two or more binding partners. The scaffold nucleic acid may be of any length sufficient to allow association (i.e., binding) and dissociation (i.e., unbinding) of binding partners to occur, to be detected, and to be distinguished from other events. In some instances, the scaffold nucleic acid is at least 1000 nucleotides in length, and it may be as long as 20,000 nucleotides in length (or it may be longer). The scaffold nucleic acid may therefore be 1000-20,000 nucleotides in length, 2000-15,000 nucleotides in length, 5000-12,000 in length, or any range therebetween. The scaffold may be a naturally occurring nucleic acid (e.g., M13 scaffolds such as M13mp18). M13 scaffolds are disclosed by Rothemund 2006 Nature 440:297-302, the teachings of which are incorporated by reference herein. The scaffold nucleic acid may be lambda DNA, in other embodiments. The scaffold nucleic acid may also be non-naturally occurring nucleic acids such as polymerase chain reaction (PCR)-generated nucleic acids, rolling circle amplification (RCA)-generated nucleic acids, etc.

In some embodiments, the binding partners are positioned along the scaffold nucleic acid to yield loops and thus length changes that are detectable. These may include loops that are about 40-100 base pairs, or about 100-1000 base pairs, or about 500-5000 base pairs. The scaffold may be partially or fully single-stranded or partially or fully double-stranded. The complex may comprise varying lengths of double-stranded regions.

The scaffold nucleic acid may comprise DNA, RNA, DNA analogs, RNA analogs, or a combination thereof. In some instances, the binding partners are conjugated to a scaffold nucleic acid via hybridization of oligonucleotides to the scaffold, wherein such oligonucleotides are themselves conjugated to a binding partner. In some instances, the scaffold nucleic acid is a DNA.

The scaffold nucleic acid is hybridized to one, two or more, including a plurality, of oligonucleotides. Each of the plurality of oligonucleotides may hybridize to the scaffold nucleic acid in a sequence-specific and non-overlapping manner (i.e., each oligonucleotide hybridizes to a distinct sequence in the scaffold).

The number of oligonucleotides hybridized to a particular scaffold may vary depending on the application. Accordingly, there may be 2 or more oligonucleotides hybridized to the scaffold, including 3, 4, 5, 6, 7, 8, 9, 10, 20, 30, 40, 50, 60, 70, 80, 90, 100, 200, 300, 400, 500, 600, 700, 800, 900, or 1000 or more oligonucleotides.

In some instances, some oligonucleotides hybridized to the scaffold nucleic acid will be unmodified. Unmodified oligonucleotides include oligonucleotides that are not linked to binding partners such as binding partners being tested (e.g., an antibody or an antigen). In other instances, some or all the oligonucleotides hybridized to the scaffold may be modified. Modified oligonucleotides include those that are linked to binding partners being tested (e.g., a receptor and/or its ligand, an antibody and/or its antigen, etc.). Modified oligonucleotides may also include those that are modified and thus used to immobilize the nanoswitch to a solid support such as but not limited to a bead. Such modified oligonucleotides including biotinylated oligonucleotides. Modified oligonucleotides may be referred to herein as "variable" oligonucleotides since these oligonucleotides may be modified by linking to a variety of binding partners depending on the method of use.

Regions comprising scaffold hybridized to modified oligonucleotides may be referred to herein as "variable" regions and the remaining scaffold regions may be referred to as "fixed" regions.

The spacing of binding partners, and thus in some instances of the modified (or variable) oligonucleotides, along the length of the scaffold nucleic acid may vary. In some embodiments, the nanoswitch may comprise three or four binding partners, and thus in some embodiments variable regions (e.g., three or four modified oligonucleotides). As an example, a nucleic acid nanoswitch may comprise modified oligonucleotides at one or both of its ends as well as two internal modified oligonucleotides. The modified oligonucleotides at the ends of the nanoswitch may be used to immobilize the nanoswitch to a solid support such as a bead. The modified oligonucleotides internal to the nanoswitch may be linked individually to members of a binding pair (i.e., each of the two oligonucleotides is linked to a member of the binding pair such that the nanoswitch comprises the binding pair, with each member of the pair on a different oligonucleotide). The internal modified oligonucleotides may be symmetrically or quasi-symmetrically located around the center of the scaffold. In other words, they may be positioned equi-distant from the center of the scaffold.

In some embodiments, the invention contemplates the use of a plurality of nanoswitches each comprising the same binding pair. The difference between the nanoswitches in the plurality is the distance between the binding pair members (i.e., the binding partners). For example, the plurality may comprise nanoswitches in which the distance between the binding pair members is 300 base pairs, 200 base pairs, 150 base pairs, 100 base pairs, 80 base pairs, 60 base pairs, and 40 base pairs. The nanoswitches are then analyzed for their ability to form looped structures based on interaction between the binding partners. It is expected that as the distance between the binding partners decreases, a greater internal force is exerted on the binding interaction. Accordingly, the binding interaction will continue until the internal force becomes too great and the complex assumes the more energetically favorable linear state. The kinetics and strength of a binding interaction between two binding partners can be analyzed using this approach.

Importantly, the distance between the binding partners will be used to distinguish association and dissociation between binding partners linked to the nanoswitches. This is because when the binding partners are associated with each other, a loop will be formed comprising the nucleic acid sequence that exists between the binding partners. When the binding partners are not associated to each other (i.e., unbound), then the loop does not form and the complex length is different (i.e., longer). The nanoswitch length may be detected by direct measurements, for example, under tension, as described herein. When measured under tension, the transition from associated to dissociated binding partners is indicated by an increase in length of the nanoswitch.

The ability to distinguish loops of differing sizes (and thus changes of length of different magnitudes) facilitates the use of multiple nanoswitches in a single assay where one or subsets of nanoswitches (all having the same loop size) are specific for a particular molecular interaction, including for example binding to a particular analyte in a sample. In these aspects, the binding partners bound to the nanoswitch do not bind to each other but rather bind to an analyte. Accordingly, in the presence of the analyte a loop is formed while in the absence of the analyte no loop is formed. The looped (or closed or bound) nanoswitch has a shorter length than the linear (or open or unbound) nanoswitch. Additionally, loops of different sizes (and thus changes in lengths) can be distinguished from each other and as a result the presence (or absence) of a multiple analytes (each detected by a nanoswitch having a loop of a particular size, and thus a particular change in length) can be determined simultaneously in a multiplexed assay. Such methods may be used to detect the presence of a single or multiple analytes and may form the basis of a diagnostic assay.

It is to be understood that several variations on the nucleic acid nanoswitches described herein. Typically, these variations all commonly comprise a nucleic acid nanoswitches having two or more binding partners. The binding partners may have binding specificity for each other or they may have binding specificity for a common analyte. Several of the methods rely on the association and/or dissociation of binding partners. A change in length of the nanoswitch (e.g., from an open to a closed conformation or from a closed to an open conformation) provides information about the kinetics and strength of the binding interaction. The binding partners may be non-covalently or covalently bound to the complex. Typically, even if the binding partners are not bound to each other, they are nevertheless bound to the nucleic acid nanoswitch.

Thus, in a first variation, the nucleic acid nanoswitches comprises two binding partners having binding specificity for each other. The binding partners are physically separate and thus spaced apart from each other along the length of the nanoswitch backbone (i.e., when not bound to each other). When bound to each other, the nucleic acid nanoswitch assumes a looped (or closed or bound) conformation having a different length, compared to the nucleic acid nanoswitch in an open (or unbound) conformation.

In another variation, the nucleic acid complex comprises two binding partners having binding specificity for a common analyte. The binding partners are physically separate and thus spaced apart from each other (when not bound to the common analyte). When bound to the common analyte, the nucleic acid nanoswitch assumes a looped (or closed or bound) conformation having a different length, compared to the nucleic acid nanoswitch in an open (or unbound) conformation.

The invention further contemplates that a nucleic nanoswitches may comprise more than two linked binding partners. The number of binding partners may be 2, 3, 4, 5, or more. In some embodiments, pairs of binding partners are provided, with each pair having binding specificity for each other (i.e., rather than binding specificity for a common analyte). In some embodiments, three binding partners may be provided such that two binding partners compete for binding of the remaining binding partner. The location or arrangement of the binding partners may vary and may include serially positioned binding pairs or nested binding pairs, or combinations thereof. As an example, assume that A1 and A2 are a binding pair (e.g., first and second binding partners) and B1 and B2 are a different binding pair (e.g., third and fourth binding partners), then these may be arranged as 5'-A1-A2-B1-B2-3', or they may be arranged as 5'-A1-B1-B2-A2-3'.

The nanoswitches comprise binding partners such as for example an antibody or an antigen. The linkage between the nucleic acid and the binding partner may be covalent or non-covalent depending on the strength of binding required for a particular application. They may be generated by first incorporating a reactive group (or moiety) into the nucleic acid (or into an oligonucleotide hybridized to the nucleic acid), and then reacting this group (or moiety) with the binding partner of interest which may or may not be modified itself. Suitable reactive groups are known in the art. Examples of reactive groups that can covalently conjugate to other reactive groups (leading to an irreversible conjugation) include but are not limited to amine groups (which react to, for example, esters to produce amides), carboxylic acids, amides, carbonyls (such as aldehydes, ketones, acyl chlorides, carboxylic acids, esters and amides) and alcohols. Those of ordinary skill in the art will be familiar with other "covalent" reactive groups. Examples of reactive groups that non-covalently conjugate to other molecules (leading to a reversible conjugation) include biotin and avidin or streptavidin reactive groups (which react with each other), antibody (or antibody fragment) reactive groups and antigens, receptors and receptor ligands, aptamers and aptamer ligands, nucleic acids and their complements, and the like. Virtually any reactive group is amenable to the methods of the invention, provided it participates in an interaction of sufficient affinity to prevent dissociation of the binding partner from the nucleic acid nanoswitch.

It is to be understood that the scaffold nucleic acid and if used the oligonucleotides may be DNA or RNA in nature, or some combination thereof, or some analog or derivative thereof. The term nucleic acid refers to a polymeric form of nucleotides of any length, including deoxyribonucleotides, ribonucleotides, or analogs thereof. In some embodiments, the nucleic acids will be DNA in nature, and may optionally comprise modifications at their 5' end and/or their 3' end.

In some embodiments, the binding partners may include without limitation antibodies (or antibody fragments) and antigens, receptors and ligands, aptamers and aptamer receptors, nucleic acids and their complements, and the like. This list is not intended to be limited or exhaustive and other binding partners will be apparent and may be used in conjunction with the nanoswitches described herein.

Example

Tethered particle motion analysis was carried out for tethered beads prior to the rupture force measurement. The lateral fluctuations of each bead were analyzed, calculating the root mean square of the drift-subtracted displacement and the symmetry ratio, following previously established methods[33]. Here, the symmetry ratio was calculated as the square root of the ratio between the minimum and maximum eigenvalues of the covariance matrix for the in-plane displacement. The in-plane position of each bead was recorded for 10 seconds at an acquisition rate of 10 Hz.

It should be understood that the foregoing description is intended merely to be illustrative thereof and that other embodiments, modifications, and equivalents are within the scope of the present disclosure recited in the claims appended hereto. Further, although each embodiment described above includes certain features, the present disclosure is not limited in this respect. Thus, one or more of the above-described or other features of the implantable device or methods of use, may be employed singularly or in any suitable combination, as the present disclosure and the claims are not limited to a specific embodiment.

REFERENCES

1. Bustamante C, Cheng W, Meija Y X. Revisiting the Central Dogma One Molecule at a Time. *Cell* 144, 480-497 (2011).
2. Neuman K C, Nagy A. Single-molecule force spectroscopy: optical tweezers, magnetic tweezers and atomic force microscopy. *Nat Methods* 5, 491-505 (2008).
3. Ritort F. Single-molecule experiments in biological physics: methods and applications. *J Phys-Condens Mat* 18, R531-R583 (2006).
4. Bustamante C J, Kaiser C M, Maillard R A, Goldman D H, Wilson C A M. Mechanisms of Cellular Proteostasis: Insights from Single-Molecule Approaches. *Annual Review of Biophysics, Vol 43* 43, 119-140 (2014).
5. Greenleaf W J, Woodside M T, Block S M. High-resolution, single-molecule measurements of biomolecular motion. *Annual review of biophysics and biomolecular structure* 36, 171 (2007).
6. Sitters G, Kamsma D, Thalhammer G, Ritsch-Marte M, Peterman E J G, Wuite G J L. Acoustic force spectroscopy. *Nat Methods* 12, 47-50 (2015).
7. Soltani M, et al. Nanophotonic trapping for precise manipulation of biomolecular arrays. *Nat Nanotechnol* 9, 448-452 (2014).
8. De Vlaminck I, et al. Highly Parallel Magnetic Tweezers by Targeted DNA Tethering. *Nano Letters* 11, 5489-5493 (2011).
9. Fazio T, Visnapuu M L, Wind S, Greene E C. DNA curtains and nanoscale curtain rods: High-throughput tools for single molecule imaging. *Langmuir* 24, 10524-10531 (2008).
10. Ribeck N, Saleh O A. Multiplexed single-molecule measurements with magnetic tweezers. *Rev Sci Instrum* 79, (2008).
11. Kim S J, Blainey P C, Schroeder C M, Xie X S. Multiplexed single-molecule assay for enzymatic activity on flow-stretched DNA. *Nat Methods* 4, 397-399 (2007).
12. Otten M, et al. From genes to protein mechanics on a chip. *Nature methods* 11, 1127-1130 (2014).
13. Chiou P Y, Ohta A T, Wu M C. Massively parallel manipulation of single cells and microparticles using optical images. *Nature* 436, 370-372 (2005).
14. Evans E. Probing the relation between force-lifetime-and chemistry in single molecular bonds. *Annual review of biophysics and biomolecular structure* 30, 105-128 (2001).
15. Kim J, Zhang C-Z, Zhang X, Springer T A. A mechanically stabilized receptor-ligand flex-bond important in the vasculature. *Nature* 466, 992-995 (2010).
16. Li P T, Bustamante C, Tinoco I. Unusual mechanical stability of a minimal RNA kissing complex. *Proceedings of the National Academy of Sciences* 103, 15847-15852 (2006).
17. Halvorsen K, Schaak D, Wong W P. Nanoengineering a single-molecule mechanical switch using DNA self-assembly. *Nanotechnology* 22, (2011).
18. Halvorsen K, Wong W P. Massively parallel single-molecule manipulation using centrifugal force. *Biophysical journal* 98, L53-L55 (2010).
19. Harvey E N, Loomis A L. A microscope-centrifuge. *Science* 72, 42-44 (1930).

20. Oiwa K, Chaen S, Kamitsubo E, Shimmen T, Sugi H. Steady-state force-velocity relation in the ATP-dependent sliding movement of myosin-coated beads on actin cables in vitro studied with a centrifuge microscope. *Proceedings of the National Academy of Sciences* 87, 7893-7897 (1990).
21. Koussa M A, Halvorsen K, Ward A, Wong W P. DNA nanoswitches: a quantitative platform for gel-based biomolecular interaction analysis. *Nat Methods* 12, 123-U148 (2015).
22. Cheng W, Arunajadai S G, Moffitt J R, Tinoco I, Bustamante C. Single-base pair unwinding and asynchronous RNA release by the hepatitis C virus NS3 helicase. *Science* 333, 1746-1749 (2011).
23. Yu Z, et al. Tertiary DNA structure in the single-stranded hTERT promoter fragment unfolds and refolds by parallel pathways via cooperative or sequential events. *Journal of the American Chemical Society* 134, 5157-5164 (2012).
24. Baumann C G, Smith S B, Bloomfield V A, Bustamante C. Ionic effects on the elasticity of single DNA molecules. *P Natl Acad Sci USA* 94, 6185-6190 (1997).
25. Lee C H, Danilowicz C, Conroy R S, Coljee V W, Prentiss M. Impacts of magnesium ions on the unzipping of gimel-phage DNA. *J Phys-Condens Mat* 18, S205-S213 (2006).
26. Mao H, Arias-Gonzalez J R, Smith S B, Tinoco I, Bustamante C. Temperature control methods in a laser tweezers system. *Biophysical journal* 89, 1308-1316 (2005).
27. Williams M C, Wenner J R, Rouzina I, Bloomfield V A. Entropy and heat capacity of DNA melting from temperature dependence of single molecule stretching. *Biophysical Journal* 80, 1932-1939 (2001).
28. Stephenson W, et al. Combining temperature and force to study folding of an RNA hairpin. *Physical Chemistry Chemical Physics* 16, 906-917 (2014).
29. Danilowicz C, Kafri Y, Conroy R S, Coljee V W, Weeks J, Prentiss M. Measurement of the phase diagram of DNA unzipping in the temperature-force plane. *Physical Review Letters* 93, (2004).
30. Rief M, Clausen-Schaumann H, Gaub H E. Sequence-dependent mechanics of single DNA molecules. *Nature Structural & Molecular Biology* 6, 346-349 (1999).
31. Zhang X, Halvorsen K, Zhang C-Z, Wong W P, Springer T A. Mechanoenzymatic cleavage of the ultralarge vascular protein von Willebrand factor. *Science* 324, 1330-1334 (2009).
32. Lipfert J, Kerssemakers J W J, Jager T, Dekker N H. Magnetic torque tweezers: measuring torsional stiffness in DNA and RecA-DNA filaments. *Nat Methods* 7, 977-U954 (2010).
33. Nelson P C, Zurla C, Brogioli D, Beausang J F, Finzi L, Dunlap D. Tethered particle motion as a diagnostic of DNA tether length. *The Journal of Physical Chemistry B* 110, 17260-17267 (2006).
34. Danilowicz, C. et al. Measurement of the phase diagram of DNA unzipping in the temperature-force plane. *Phys Rev Lett* 93, doi:Doi 10.1103/Physrevlett.93.078101 (2004).
35. De Vlaminck, I. & Dekker, C. Recent advances in magnetic tweezers. *Annual review of biophysics* 41, 453-472 (2012).
36. Halvorsen, K., Schaak, D. & Wong, W. P. Nanoengineering a single-molecule mechanical switch using DNA self-assembly. *Nanotechnology* 22, doi:Doi 10.1088/0957-4484/22/49/494005 (2011).
37. Koussa, M. A., Halvorsen, K., Ward, A. & Wong, W. P. DNA nanoswitches: a quantitative platform for gel-based biomolecular interaction analysis. *Nat Methods* 12, 123-U148, doi:Doi 10.1038/Nmeth.3209 (2015).

What is claimed is:

1. An apparatus for measuring a characteristic of a sample, the apparatus being a spinning force system, and comprising:
   a module comprising:
   a sample holder;
   a light source configured to illuminate the sample;
   an imaging axis oriented along a direction at which light from the light source hits the sample holder; and a detector configured to receive light from the light source, wherein the module is sized and dimensioned to fit within a centrifuge receptacle having a volume of less than or equal to 1 L, and wherein the spinning force system is arranged such that a direction of centrifugal force applied to the sample holder by a centrifuge and the imaging axis are misaligned in order to track lateral particle motion.

2. The apparatus of claim 1, wherein the volume is of less than or equal to 400 mL.

3. The apparatus of claim 1, wherein the sample holder, light source and detector are physically misaligned.

4. The apparatus of claim 3, wherein module further comprises at least one mirror that directs light from the light source to the sample holder or to the detector.

5. The apparatus of claim 3, wherein the sample holder and light source are aligned along a line and the detector is misaligned from the line.

6. The apparatus of claim 5, wherein the module forms a U-shape having a first leg and a second leg.

7. The apparatus of claim 6, wherein the sample holder and light source are positioned within the first leg and the detector is positioned within the second leg.

8. The apparatus of claim 6, wherein the first leg is longer than the second leg.

9. The apparatus of claim 1, wherein the module further comprises an objective.

10. The apparatus of claim 9, wherein the sample holder, light source and objective are aligned along a line and the detector is misaligned from the line.

11. A method comprising:
attaching a particle to a surface through a molecular interaction associated with a first molecule and a second molecule;
rotating the surface about an axis of rotation to apply a centrifugal force to the particle, the centrifugal force having a direction;
hitting the particle with light from a light source;
detecting an image of the particle with a detector during rotation of the surface, the image containing information representing a characteristic of the molecular interaction; and
determining the characteristic of the molecular interaction based on the detected image, wherein an imaging axis is angled relative to the direction of the centrifugal force, the imaging axis being oriented along the direction at which light from the light source hits the particle to permit tracking of lateral particle motion.

12. The method of claim 11, wherein the surface is held within a centrifugal bucket, and the bucket is at an oblique angle relative to the axis of rotation.

13. The method of claim 11, wherein:
the step of attaching a particle to a surface comprises attaching a nucleic acid nanoswitch to the surface, wherein the nucleic acid nanoswitch comprises a nucleic acid conjugated to the particle on its free end.

14. The method of claim 11, further comprising:
inserting the surface into a centrifuge; and
selecting a centrifuge temperature using a temperature control built into the centrifuge.

15. The method of claim 14, further comprising:
changing the centrifuge temperature using the temperature control built into the centrifuge.

16. The method of claim 11, wherein:
the step of rotating the surface about the axis of rotation comprises rotating the surface a first time; after rotating the surface the first time, stopping rotation of the surface; and after stopping rotation of the surface, rotating the surface a second time to apply a force to the particle;
the step of detecting an image of the particle comprises detecting images of the particle during rotation of the surface the first time and the second time, the images containing information representing a characteristic of the molecular interaction; and
the step of determining the characteristic of the molecular interaction comprises determining the characteristic of the molecular interaction based on the detected images.

17. The apparatus of claim 1, further comprising the centrifuge.

* * * * *